(12) United States Patent
Light et al.

(10) Patent No.: US 11,504,417 B2
(45) Date of Patent: Nov. 22, 2022

(54) BLOOD SUBSTITUTES COMPRISING HEMOGLOBIN AND METHODS OF MAKING

(71) Applicant: VIRTECH BIO, INC., Natick, MA (US)

(72) Inventors: William Richard Light, Natick, MA (US); Joseph Tucker, Natick, MA (US)

(73) Assignee: VIRTECH BIO, INC., Natick, MA (US)

( * ) Notice: Subject to any disclaimer, the term of this patent is extended or adjusted under 35 U.S.C. 154(b) by 0 days.

(21) Appl. No.: 16/632,090

(22) PCT Filed: Jul. 17, 2018

(86) PCT No.: PCT/US2018/042497
§ 371 (c)(1),
(2) Date: Jan. 17, 2020

(87) PCT Pub. No.: WO2019/018403
PCT Pub. Date: Jan. 24, 2019

(65) Prior Publication Data
US 2020/0222510 A1    Jul. 16, 2020

Related U.S. Application Data

(60) Provisional application No. 62/534,000, filed on Jul. 18, 2017.

(51) Int. Cl.
*A61K 38/42* (2006.01)
*A61P 7/08* (2006.01)
*A61K 9/00* (2006.01)
*C12N 5/078* (2010.01)

(52) U.S. Cl.
CPC ............ *A61K 38/42* (2013.01); *A61K 9/0026* (2013.01); *A61P 7/08* (2018.01); *C12N 5/0641* (2013.01)

(58) Field of Classification Search
None
See application file for complete search history.

(56) References Cited

U.S. PATENT DOCUMENTS

| | | | |
|---|---|---|---|
| 4,336,248 A * | 6/1982 | Bonhard | C07K 14/805 514/13.4 |
| 4,401,652 A * | 8/1983 | Simmonds | C07K 14/805 514/13.4 |
| 4,526,715 A * | 7/1985 | Kothe | C07K 14/805 530/385 |
| 4,529,719 A * | 7/1985 | Tye | C07K 14/805 514/13.4 |
| 4,532,130 A | 7/1985 | Djordjevich et al. | |
| 5,128,452 A | 7/1992 | Hai et al. | |
| 5,189,146 A | 2/1993 | Hsia | |
| 5,194,590 A | 3/1993 | Sehgal et al. | |
| 5,248,766 A | 9/1993 | Nelson et al. | |
| 5,281,579 A | 1/1994 | Estep | |
| 5,290,919 A | 3/1994 | Bucci et al. | |
| 5,295,944 A | 3/1994 | Teicher et al. | |
| 5,334,705 A | 8/1994 | Bonaventura et al. | |
| 5,349,054 A | 9/1994 | Bonaventura et al. | |
| 5,362,855 A | 11/1994 | Garlick et al. | |
| 5,387,672 A | 2/1995 | Bucci | |
| 5,439,882 A | 8/1995 | Feola et al. | |
| 5,563,047 A | 10/1996 | Petersen | |
| 5,646,252 A | 7/1997 | Antonius | |
| 5,679,638 A | 10/1997 | Teicher et al. | |
| 5,691,452 A | 11/1997 | Gawryl et al. | |
| 5,691,453 A | 11/1997 | Wertz et al. | |
| 5,733,869 A | 3/1998 | Burhop et al. | |
| 5,741,894 A | 4/1998 | Azari et al. | |
| 5,753,616 A | 5/1998 | Rausch et al. | |

(Continued)

FOREIGN PATENT DOCUMENTS

| | | |
|---|---|---|
| JP | 2004-521088 A | 7/2004 |
| JP | 2008-534067 A | 8/2008 |

(Continued)

OTHER PUBLICATIONS

Sakai, H et al., "Encapsulation of Concentrated Hemoglobin Solution in Phospholipid Vesicles Retards the Reaction with NO but Not CO, by Intracellular Diffusion Barrier". The Journal of Biological Chemistry, vol. 283, No. 3, pp. 1508-1517. (2008).
International Search Report and Written Opinion issued in corresponding International Application No. PCT/US19/055797; dated Feb. 10, 2020 (23 pages).
International Search Report and Written Opinion in corresponding PCT Application No. PCT/US2018/042497 (26 pages).
Y. Bian, et al., "Polyhemoglobin-superoxide Dismutase-catalase-carbonic Anhydrase: A Novel Biotechnology-based Blood Substitute that Transports both Oxygen and Carbon Dioxide and also Acts as an Antioxidant", Artif. Cells Blood Substit. Immobil. Biotechnol., 39(3), pp. 127-136 (2011).
R. Thuillier, et al., "Supplementation With a New Therapeutic Oxygen Carrier Reduces Chronic Fibrosis and Organ Dysfunction in Kidney Static Preservation", American Journal of Transplantation, 11, pp. 1845-1860 (2011).

(Continued)

*Primary Examiner* — Anand U Desai
(74) *Attorney, Agent, or Firm* — Venable LLP

(57) ABSTRACT

Methods for making hemoglobin based blood substitute preparations and hemoglobin based blood substitute preparations. The methods involve preparing a low purity erythrocyte protein fraction comprising hemoglobin protein and endogenous non-hemoglobin protein complement, and chemically modifying the proteins in the protein fraction to form a cross-linked hemoglobin containing blood substitute preparation. The low purity erythrocyte protein preparation can contain from at least about 0.2% (mole/mole) up to about 20% (mole/mole) endogenous non-hemoglobin protein complement. At least about 90% (mole/mole) of the hemoglobin proteins can be cross-linked, so that the average molecular mass of cross-linked proteins comprising hemoglobin protein molecules in the preparation is at least about 300 kDa. The preparations can be used to prepare finished blood substitute formulations for in-vivo and ex-vivo use.

16 Claims, 15 Drawing Sheets

(56) References Cited

U.S. PATENT DOCUMENTS

| | | |
|---|---|---|
| 5,747,649 A | 6/1998 | Sehgal et al. |
| 5,789,376 A | 8/1998 | Hsia |
| 5,804,551 A | 9/1998 | Burhop |
| 5,811,521 A | 9/1998 | Kluger et al. |
| 5,833,974 A | 11/1998 | Feicher |
| 5,843,888 A | 12/1998 | Ho et al. |
| 5,854,210 A | 12/1998 | Burhop |
| 5,895,810 A | 4/1999 | Light et al. |
| 5,906,974 A | 5/1999 | Blue et al. |
| 5,952,470 A | 9/1999 | Light et al. |
| 5,970,985 A | 10/1999 | Burhop et al. |
| 5,981,710 A | 11/1999 | Hai et al. |
| 5,985,332 A | 11/1999 | Bamikol et al. |
| 5,985,825 A | 11/1999 | Winslow et al. |
| 5,998,361 A | 12/1999 | Bucci et al. |
| 6,046,170 A | 4/2000 | Burhop et al. |
| 6,054,427 A | 4/2000 | Winslow |
| 6,083,909 A | 7/2000 | Sommermeyer et al. |
| 6,117,838 A | 9/2000 | Przybelski |
| 6,160,098 A | 12/2000 | Kerwin et al. |
| 6,180,598 B1 | 1/2001 | Nelson |
| 6,284,481 B1 | 9/2001 | Rane et al. |
| 6,416,736 B1 | 7/2002 | Bepperling et al. |
| 6,458,762 B1 | 10/2002 | McKenzie et al. |
| 6,479,637 B1 | 11/2002 | Adamson et al. |
| 6,486,123 B1 | 11/2002 | Ho et al. |
| 6,498,141 B2 | 12/2002 | DeWoskin et al. |
| 6,500,930 B2 | 12/2002 | Adamson |
| 6,518,010 B2 | 2/2003 | Gawryl et al. |
| 6,566,326 B1 | 5/2003 | Soltero et al. |
| 6,623,972 B2 | 9/2003 | Malin et al. |
| 6,773,613 B1 | 8/2004 | Winslow et al. |
| 6,780,892 B1 | 8/2004 | Fronticelli |
| 6,811,778 B2 | 11/2004 | Page et al. |
| 6,956,025 B2 | 10/2005 | Bamikol |
| 6,974,794 B1 | 12/2005 | Adamson et al. |
| 6,986,984 B2 | 1/2006 | Gawryl et al. |
| 7,001,715 B2 | 2/2006 | Houtchens et al. |
| 7,005,414 B2 | 2/2006 | Bamikol et al. |
| 7,019,117 B2 | 3/2006 | Acharya et al. |
| 7,038,016 B2 | 5/2006 | Talarico et al. |
| 7,135,553 B2 | 11/2006 | Avella et al. |
| 7,135,554 B1 | 11/2006 | Page et al. |
| 7,144,989 B2 | 12/2006 | Acharya et al. |
| 7,202,341 B2 | 4/2007 | McGinnis et al. |
| 7,211,560 B2 | 5/2007 | Looker et al. |
| 7,267,817 B2 | 9/2007 | Page et al. |
| 7,271,145 B2 | 9/2007 | Winslow et al. |
| 7,291,592 B2 | 11/2007 | Gould et al. |
| 7,329,641 B2 | 2/2008 | Fronticelli |
| 7,411,044 B2 | 8/2008 | Avella et al. |
| 7,435,795 B2 | 10/2008 | McGinnis et al. |
| 7,459,535 B2 | 12/2008 | Page et al. |
| 7,494,974 B2 | 2/2009 | Tye |
| 7,521,417 B2 | 4/2009 | DeWoskin et al. |
| 7,553,613 B2 | 6/2009 | Gawryl et al. |
| 7,598,220 B2 | 10/2009 | Bamikol |
| 7,622,439 B2 | 11/2009 | Winslow et al. |
| 7,759,306 B2 | 7/2010 | Simoni et al. |
| 7,932,356 B1 | 4/2011 | Wong et al. |
| 8,021,858 B2 | 9/2011 | Vandegriff et al. |
| 8,084,581 B1 | 12/2011 | Wong et al. |
| 8,106,011 B1 | 1/2012 | Wong et al. |
| 8,420,381 B2 | 4/2013 | Owen et al. |
| 8,609,814 B2 | 12/2013 | Cooper |
| 8,609,815 B2 | 12/2013 | Vandegriff et al. |
| 8,697,645 B2 | 4/2014 | Acharya et al. |
| 8,742,073 B2 | 6/2014 | Wong et al. |
| 8,846,306 B2 | 9/2014 | Zal et al. |
| 8,889,830 B2 | 11/2014 | Komatsu et al. |
| 9,066,933 B2 | 6/2015 | Wong et al. |
| 10,029,001 B2 * | 7/2018 | Vandegriff ................ A61P 9/14 |
| 2002/0164379 A1 | 11/2002 | Nishihara et al. |
| 2003/0125238 A1 | 7/2003 | Adamson |
| 2003/0171260 A1 | 9/2003 | Nelson |
| 2004/0023851 A1 | 2/2004 | Barnikol |
| 2004/0072729 A1 | 4/2004 | Kwang et al. |
| 2004/0242846 A1 | 12/2004 | Bamikol |
| 2005/0129747 A1 | 6/2005 | Bamikol et al. |
| 2006/0182807 A1 | 8/2006 | Vauthier et al. |
| 2006/0247423 A1 | 11/2006 | Su et al. |
| 2007/0265195 A1 | 5/2007 | Freilich |
| 2007/0142626 A1 | 6/2007 | Kluger et al. |
| 2008/0069771 A1 | 3/2008 | Laccetti et al. |
| 2008/0096805 A1 | 4/2008 | Tye |
| 2008/0138790 A1 | 6/2008 | Winslow et al. |
| 2009/0215670 A1 | 8/2009 | Acharya et al. |
| 2010/0035798 A1 | 2/2010 | Sen et al. |
| 2010/0144595 A1 | 6/2010 | Bucci et al. |
| 2010/0144597 A1 | 6/2010 | Ward et al. |
| 2010/0145298 A1 | 6/2010 | Hori et al. |
| 2010/0209518 A1 | 8/2010 | Georgieva |
| 2010/0209532 A1 | 8/2010 | Dube et al. |
| 2012/0052136 A1 | 3/2012 | Rousselot et al. |
| 2012/0196270 A1 | 8/2012 | Young et al. |
| 2013/0115169 A1 | 5/2013 | Lahann et al. |
| 2013/0217860 A1 | 8/2013 | Malavalli et al. |
| 2014/0221944 A1 | 8/2014 | Sander et al. |
| 2014/0227677 A1 | 8/2014 | Dube |
| 2014/0323403 A1 | 10/2014 | Platt |
| 2014/0335018 A1 | 11/2014 | Wong et al. |
| 2014/0371149 A1 | 12/2014 | Sander |
| 2015/0017146 A1 | 1/2015 | Acharya et al. |
| 2015/0064275 A1 | 3/2015 | Poetzschke et al. |
| 2015/0087590 A1 | 3/2015 | Vandergrift et al. |
| 2015/0094267 A1 | 4/2015 | Vandergrift et al. |
| 2015/0031599 A1 | 8/2015 | Abuchowski et al. |

FOREIGN PATENT DOCUMENTS

| | | |
|---|---|---|
| JP | 2009-529923 A | 8/2009 |
| WO | 199107190 A1 | 5/1991 |
| WO | 199735883 A1 | 10/1997 |
| WO | 200244214 A1 | 6/2002 |
| WO | 2006104820 A1 | 10/2005 |
| WO | 2006108684 A1 | 10/2006 |
| WO | 2013016598 A2 | 3/2013 |
| WO | 2014059316 A1 | 4/2014 |
| WO | 2014145755 A1 | 9/2014 |
| WO | 2014179793 A1 | 11/2014 |
| WO | 2015042602 A1 | 3/2015 |
| WO | 2018053634 A1 | 3/2018 |

OTHER PUBLICATIONS

M. Moini, et al., "Analysis of Carbonic Anhydrase in Human Red Blood Cells Using Capillary Electrophoresis/Electrospray Ionization-Mass Spectrometry", Anal. Chem., 74(15), pp. 3772-3776 (2002).

Harris et al., "Modern Cross-Linking Strategies for Synthesizing Acellular Hemoglobin-Based Oxygen Carriers," Biotechnology Progress, vol. 24, No. 6, pp. 1215-1225 (2008).

Japanese Office Action for Japanese Patent Application 2020-524720; dated Aug. 1, 2022; includes English Translation.

Expanded European Search Report and Written Opinion for European Patent Application 18835666; dated Mar. 9, 2021.

Fischer et al., "Plasma volume expansion with solutions of hemoglobin, albumin, and Ringer lactate in sheep", American Journal of Physiology Heart and Circulatory Physiology, (Jun. 1, 1999), vol. 276, No. 6, pp. H2194-H2203.

Page et al., "Oxygen transport by erythrocyte/hemoglobin solution mixtures in an in vitro capillary as a model of hemoglobin-based oxygen carrier performance", Microvascular Research, Academic Press, (Jan. 1, 1998), vol. 55, pp. 54-64.

Extended European Search Report for EP Application 19870597.2, dated Jul. 13, 2022.

\* cited by examiner

BLOOD SUBSTITUTES COMPRISING HEMOGLOBIN AND METHODS OF MAKING

RELATED APPLICATION

This Patent Cooperation Treaty application claims the benefit under 35 USC § 119 (e) from U.S. Provisional Patent Application No. 62/534,000, filed on Jul. 18, 2017, which is incorporated by reference herein in its entirety.

FIELD OF THE DISCLOSURE

The present disclosure generally relates to blood substitutes and methods of making blood substitutes, particularly hemoglobin-based blood substitutes.

BACKGROUND

The following paragraphs are provided by way of background to the present disclosure. They are not however an admission that anything discussed therein is prior art or part of the knowledge of persons skilled in the art.

There are many circumstances in which media for oxygen transport compatible with living organisms and organs are useful. For example, whole blood or blood fractions may be used in emergency treatment of accident victims, or during the performance of surgical procedures, to deliver oxygen to the peripheral tissues of a patient, e.g. liver, kidney, and lung, in order to ensure a continued adequate oxygen supply. Conversely, when an organ becomes insufficiently oxygenated to satisfy its needs, anemic hypoxia leads to cell damage and eventually to cell and tissue death. Blood and blood fractions may also be used ex-vivo to perfuse organs and tissue intended for clinical organ or tissue transplantation. However due to blood donor shortages and safety concerns associated with blood-borne pathogenic agents, blood supply frequently falls short of the requirements, especially in developing countries. Thus, it is well understood that media capable of carrying and delivering adequate quantities of oxygen to living organisms or tissues without undue side effects are highly desirable.

In order to address the foregoing need, several techniques for preparing blood substitutes, mimicking the inherent oxygen carrying characteristics of blood, have evolved. One set of techniques known to the art involves the preparation of red blood cells, also known as erythrocytes, containing the oxygen carrying protein hemoglobin. There are however significant drawbacks associated with the use of erythrocyte preparations as blood substitutes, including the presence of contagious blood-borne disease contaminants, e.g. hepatitis B and human immunodeficiency virus (HIV), the lack of availability of specific blood types, and the inability to store such erythrocyte preparations for prolonged periods of time.

In order to overcome the foregoing drawbacks, alternate development efforts have been directed to obtaining pure preparations of hemoglobin for use as a blood substitute. However, when hemoglobin preparations first became available for clinical evaluation, it became apparent that they were unsuitable since they caused severe nephrotoxicity which was attributed to the presence of erythrocyte stroma lipids in these preparations. Methodologies were then developed to remove stroma lipids, and while addressing nephrotoxicity, stroma lipid-free hemoglobin preparations exhibited suboptimal oxygen delivery characteristics, and furthermore a significantly reduced vascular half-life. These shortcomings in turn led to the development of hemoglobin derivatives known as hemoglobin based oxygen carriers (also commonly referred to as HBOCs) for use as blood substitutes. The manufacture of HBOC preparations generally involves obtaining a highly pure hemoglobin solution and subsequent cross-linking of hemoglobin oligomers to obtain a preparation containing polymeric hemoglobin.

One particular limitation of existing HBOC manufacturing methodologies known to the art is that they involve the manufacture of highly purified hemoglobin preparations. The requirement for highly purified hemoglobin preparations imparts an extraordinary complexity on the manufacturing processes for HBOC preparations, and the costs associated with the construction of manufacturing facilities and operation of known manufacturing processes for highly pure HBOC preparations, renders known HBOC manufacturing processes substantially uneconomical.

One further particular limitation of many existing HBOC manufacturing methodologies is that the known hemoglobin polymerization techniques involve the use of the chemical reactant sodium borohydride ($BH_4^-$), an agent which is particularly impractical to employ in larger scale manufacturing processes in view of the fact that its chemical reaction results in the release of hydrogen gas. In order to restrict the risks associated with the presence of hydrogen gas in an HBOC manufacturing facility, HBOC manufacturers are required to implement carefully controlled reaction conditions, such as specialized pH conditions, and to establish elaborate safety conditions, such as flame retardant vents, and the flow of an inert gas to limit the build-up of hydrogen gas. Therefore, this represents a manufacturing step that significantly impedes the economical manufacture of HBOC products.

Yet one further particular limitation in many known HBOC manufacturing methodologies, is that in the course of the manufacturing process certain quantities of hemoglobin are converted to a variant hemoglobin known as methemoglobin. In methemoglobin the iron within the protein's heme group, which serves as the molecular binding site for oxygen, is present in the ferric ($Fe^{3+}$) state, and not in the ferrous ($Fe^{2+}$), state. Methemoglobin is unable to bind oxygen and to serve as an oxygen carrier.

Another alternate approach to providing an oxygen carrying medium known to the art involves the use of perfluro-carbon-based synthetic molecules capable of solubilizing oxygen. Synthetic carbon-fluorine molecules are chemically inert and straightforward to manufacture, however their oxygen solubility is low relative to hemoglobin, and perflurocarbon preparations are virtually immiscible with water and therefore require emulsification which render perflurocarbon preparations unstable and difficult to store.

Thus, it will be clear that even if blood substitute preparations can be obtained, many drawbacks in the manufacture techniques for such preparations remain. There is, therefore, a need in the art for improved blood substitutes and methods of making such blood substitutes, and in particular, there is a need for improved methods for making hemoglobin containing blood substitute preparations, as well as a need for economic, safe and efficacious hemoglobin containing blood substitute preparations.

SUMMARY

The following paragraphs are intended to introduce the reader to the more detailed description that follows and not to define or limit the claimed subject matter of the present disclosure.

In one broad aspect, the present disclosure relates to blood and blood substitutes.

In another broad aspect, the present disclosure relates to methods for making hemoglobin containing blood substitute preparations.

Accordingly, in one aspect, in accordance with the teachings herein, the present disclosure provides, in at least one embodiment, a method of preparing a blood substitute preparation comprising hemoglobin, the method comprising:

(i) isolating erythrocytes from blood;
(ii) isolating a low purity erythrocyte protein fraction comprising hemoglobin protein molecules and endogenous non-hemoglobin protein complement from the erythrocytes, the low purity erythrocyte protein fraction comprising from at least about 0.2% (mole/mole) up to about 20% (mole/mole) endogenous non-hemoglobin protein complement; and
(iii) contacting the low purity erythrocyte protein fraction with a reactant capable of chemically modifying the proteins in the protein fraction, the reactant thereby mediating the formation of cross-linked proteins comprising intermolecular cross-linkages between the hemoglobin protein molecules, and intermolecular cross-linkages between the hemoglobin protein molecules and the endogenous non-hemoglobin protein complement, to thereby form a blood substitute preparation.

In at least one embodiment, at least about 90% (mole/mole) of the hemoglobin protein molecules in the erythrocyte protein fraction can be cross-linked, so that the average molecular mass of cross-linked proteins is at least about 300 kDa.

In at least one embodiment, at least about 90% (mole/mole) of the hemoglobin protein molecules in the erythrocyte protein fraction can be cross-linked, so that the average molecular mass of cross-linked proteins is about 1,000 kDa.

In at least one embodiment, the endogenous non-hemoglobin protein complement can comprise carbonic anhydrase, wherein the carbonic anhydrase comprises from at least about 0.2% (mole/mole) up to about 15% (mole/mole) of the endogenous non-hemoglobin protein complement.

In at least one embodiment, the reactant capable of modifying the proteins in the erythrocyte protein fraction can be capable of forming reducible covalent cross-linkages.

In at least one embodiment, the reactant capable of modifying the proteins in the erythrocyte protein fraction can be capable of forming reducible covalent cross-linkages, wherein the reducible covalent cross-linkages are Schiff bases.

In at least one embodiment, the reactant capable of chemically modifying the proteins in the erythrocyte protein fraction can be a polyaldehyde, wherein the polyaldehyde can be reacted under reaction conditions permitting a chemical reaction between aldehyde groups of the polyaldehyde and amino groups of the proteins to form a plurality of covalent intermolecular cross-linkages between the hemoglobin protein molecules, and between the hemoglobin protein molecules and the endogenous non-hemoglobin protein complement.

In at least one embodiment, following reaction with a polyaldehyde, the cross-linked proteins can be reacted with a reducing agent to reduce the cross-linkages and form reduced cross-linkages.

In at least one embodiment, the polyaldehyde can be glutaraldehyde.

In at least one embodiment, the reducible covalent-cross-linkages can be Schiff bases, and the reduced covalent cross-linkages can be secondary amines.

In at least one embodiment, the reducing agent can be cyanoborohydride.

In at least one embodiment, the reactant capable of modifying the proteins in the erythrocyte protein fraction can be a reactant capable of intermolecularly and intramolecularly cross-linking proteins in the erythrocyte protein fraction.

In at least one embodiment, the erythrocytes can be isolated from blood by diafiltration.

In at least one embodiment, the erythrocytes can be lysed by subjecting the erythrocytes to a hypotonic shock to obtain an erythrocyte lysate from which the low purity erythrocyte protein fraction can be obtained.

In at least one embodiment, the low purity erythrocyte protein fraction can be obtained by obtaining an erythrocyte lysate from the erythrocytes and subjecting an erythrocyte lysate to membrane filtration.

In at least one embodiment, the low purity erythrocyte protein fraction can be obtained by obtaining an erythrocyte lysate from the erythrocytes and subjecting an erythrocyte lysate to tangential flow filtration.

In at least one embodiment, the method can further include the performance of a deoxygenation step, wherein the deoxygenation step is performed prior to step (i); following step (i) and prior to step (ii); following step (ii) and prior to step (iii); or following step (iii).

In another aspect, the present disclosure provides, in at least one embodiment, a method for preparing a finished blood substitute formulation comprising hemoglobin, the method comprising:

(i) providing a low purity erythrocyte protein fraction comprising hemoglobin protein molecules and endogenous non-hemoglobin protein complement obtainable from erythrocytes, the low purity erythrocyte protein fraction comprising from at least about 0.2% (mole/mole) up to about 20% (mole/mole) endogenous non-hemoglobin protein complement, the low purity erythrocyte protein fraction modified with a reactant capable of chemically modifying the proteins in the protein fraction, wherein the reactant mediates the formation of cross-linked proteins comprising intermolecular cross-linkages between the hemoglobin protein molecules and intermolecular cross-linkages between the hemoglobin protein molecules and the endogenous non-hemoglobin protein complement, to thereby form a blood substitute preparation; and
(ii) formulating the blood substitute preparation with at least one other ingredient suitable to form a finished blood substitute formulation.

In at least one embodiment, at least about 90% (mole/mole) of the hemoglobin protein molecules in the erythrocyte protein fraction can be cross-linked, so that the average molecular mass of cross-linked proteins is at least about 300 kDa.

In at least one embodiment, at least about 90% (mole/mole) of the hemoglobin protein molecules in the erythrocyte protein fraction can be cross-linked, so that the average molecular mass of cross-linked proteins is about 1,000 kDa.

In at least one embodiment, the endogenous non-hemoglobin protein complement can comprise carbonic anhydrase, wherein the carbonic anhydrase comprises from at least about 0.2% (mole/mole) up to about 15% (mole/mole) of the endogenous non-hemoglobin protein complement.

In at least one embodiment, the blood substitute preparation can be subjected to diafiltration.

In at least one embodiment, the blood substitute preparation can be subjected to diafiltration under conditions that permit the removal of proteins having a mass of less than about 300 kDa.

In at least one embodiment, the blood substitute preparation can be subjected to diafiltration under conditions that permit the removal of proteins having a mass of less than about 1,000 kDa.

In at least one embodiment, the at least one other ingredient can be an excipient, diluent or carrier.

In at least one embodiment, the finished blood substitute formulation is a formulation for in-vivo use.

In at least one embodiment, the finished blood substitute formulation is a formulation for ex-vivo use.

In another aspect, the present disclosure provides, in at least one embodiment, a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole).

In at least one embodiment, at least about 90% (mole/mole) of the hemoglobin protein molecules in the erythrocyte protein fraction can be cross-linked, so that the average molecular mass of cross-linked proteins is at least about 300 kDa.

In at least one embodiment, at least about 90% (mole/mole) of the hemoglobin protein molecules in the erythrocyte protein fraction can be cross-linked, so that the average molecular mass of cross-linked proteins is about 1,000 kDa.

In at least one embodiment, the endogenous non-hemoglobin protein complement can comprise carbonic anhydrase, wherein the carbonic anhydrase comprises from about 0.2% (mole/mole) to 15% (mole/mole) of the endogenous non-hemoglobin protein complement.

In at least one embodiment, the cross-linkages can be reducible covalent cross-linkages.

In at least one embodiment, the reducible covalent cross-linkages can be Schiff bases.

In at least one embodiment, the cross-linkages can be reduced Schiff bases.

In at least one embodiment, the cross-linkages can be reduced Schiff bases having been formed by reacting proteins in the low purity erythrocyte fraction with a polyaldehyde to form a Schiff base, and subsequent reduction of the Schiff base.

In at least some embodiments, the polyaldehyde can be glutaraldehyde.

In another aspect, the present disclosure provides, in at least one embodiment, a finished blood substitute formulation comprising a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole).

In at least one embodiment, at least about 90% (mole/mole) of the hemoglobin protein molecules in the erythrocyte protein fraction can be cross-linked, so that the average molecular mass of cross-linked proteins is at least about 300 kDa.

In at least one embodiment, at least about 90% (mole/mole) of the hemoglobin protein molecules in the erythrocyte protein fraction can be cross-linked, so that the average molecular mass of cross-linked proteins is about 1,000 kDa.

In at least one embodiment, the finished blood substitution formulation can comprise a blood substitute preparation made according to any of the methods of the present disclosure.

In another aspect, the present disclosure provides, in at least one embodiment, a use of a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole) to prepare a finished blood formulation for in-vivo use.

In at least one embodiment, at least about 90% (mole/mole) of the hemoglobin protein molecules in the erythrocyte protein fraction can be cross-linked, so that the average molecular mass of cross-linked proteins molecules is at least about 300 kDa.

In at least one embodiment, at least about 90% (mole/mole) of the hemoglobin protein molecules in the erythrocyte protein fraction can be cross-linked, so that the average molecular mass of cross-linked proteins is about 1,000 kDa.

In at least one embodiment, the blood substitute preparation can be made according to any of the methods of the present disclosure.

In at least one embodiment, the present disclosure provides a use of a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole) to prepare a finished blood formulation for ex-vivo use.

In at least one embodiment, at least about 90% (mole/mole) of the hemoglobin protein molecules in the erythrocyte protein fraction can be cross-linked, so that the average molecular mass of cross-linked proteins is at least about 300 kDa.

In at least one embodiment, at least about 90% (mole/mole) of the hemoglobin protein molecules in the erythrocyte protein fraction can be cross-linked, so that the average molecular mass of cross-linked proteins is about 1,000 kDa.

In at least one embodiment, the blood substitute preparation can be made according to any of the methods of the present disclosure.

In another aspect, the present disclosure provides, in at least one embodiment, a use of a finished blood substitute formulation comprising a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole) for in-vivo administration.

In at least one embodiment, at least about 90% (mole/mole) of the hemoglobin protein molecules in the erythrocyte protein fraction can be cross-linked, so that the average molecular mass of cross-linked proteins is at least about 300 kDa.

In at least one embodiment, at least about 90% (mole/mole) of the hemoglobin protein molecules in the erythrocyte protein fraction can be cross-linked, so that the average molecular mass of cross-linked proteins is about 1,000 kDa.

In at least one embodiment, the finished blood preparation can be in-vivo administered by injection in the circulatory system.

In at least one embodiment, the finished blood preparation can be in-vivo administered by intravenous or intra-arterial injection.

In at least one embodiment, the finished blood substitution formulation can comprise any blood substitute preparation made according to any of the methods of the present disclosure.

In at least one embodiment, the present disclosure provides, in at least one embodiment, a use of a finished blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole) for ex-vivo administration.

In at least one embodiment, at least about 90% (mole/mole) of the hemoglobin protein molecules in the erythrocyte protein fraction can be cross-linked, so that the average molecular mass of cross-linked proteins is at least about 300 kDa.

In at least one embodiment, at least about 90% (mole/mole) of the hemoglobin protein molecules in the erythrocyte protein fraction can be cross-linked, so that the average molecular mass of cross-linked proteins is about 1,000 kDa.

In at least one embodiment, the finished blood preparation can be used to ex-vivo preserve an organ or tissue.

In at least one embodiment, the finished blood preparation can be used to ex-vivo preserve an organ or tissue in static or dynamic mode.

In at least one embodiment, the finished blood substitution formulation can comprise a blood substitute preparation made according to any of the methods of the present disclosure.

In another aspect, the present disclosure provides a method of administering a therapeutically effective amount of a finished blood substitute formulation comprising a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole), to a subject in need thereof.

In at least one embodiment, at least about 90% (mole/mole) of the hemoglobin protein molecules in the erythrocyte protein fraction can be cross-linked, so that the average molecular mass of cross-linked proteins is at least about 300 kDa.

In at least one embodiment, at least about 90% (mole/mole) of the hemoglobin protein molecules in the erythrocyte protein fraction can be cross-linked, so that the average molecular mass of cross-linked proteins is about 1,000 kDa.

In at least one embodiment, the finished blood preparation can be administered by injection in the circulatory system.

In at least one embodiment, the finished blood preparation can be administered by intravenous or intra-arterial injection.

In at least one embodiment, the finished blood substitution formulation can comprise a blood substitute preparation made according to any of the methods of the present disclosure.

Other features and advantages or the present disclosure will become apparent from the following detailed description. It should be understood, however, that the detailed description, while indicating preferred implementations of the present disclosure, is given by way of illustration only, since various changes and modification within the spirit and scope of the disclosure will become apparent to those of skill in the art from the detailed description.

BRIEF DESCRIPTION OF THE DRAWINGS

For a better understanding of the various example embodiments described herein, and to show more clearly how these various embodiments may be carried into effect, reference will be made, by way of example only, to the accompanying drawings which show at least one example embodiment, and the drawings will now be briefly described.

represents a protein present in the endogenous non-hemoglobin protein complement; and "G", "G'" and "G''" represent cross-linkers.

Figure 4:
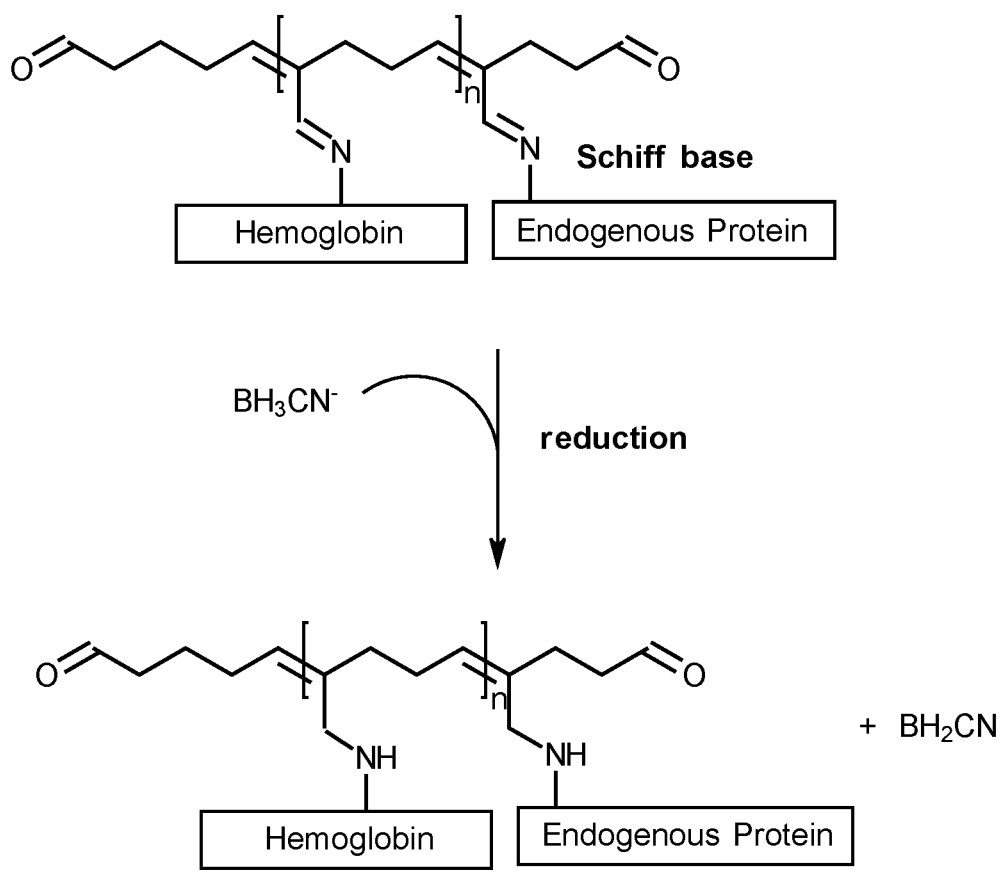

FIG. 4 depicts an example chemical reaction for reducing a Schiff base in a glutaraldehyde cross-linked protein thereby forming a secondary amine using cyanoborohydride as a reductant.

Figure 5:
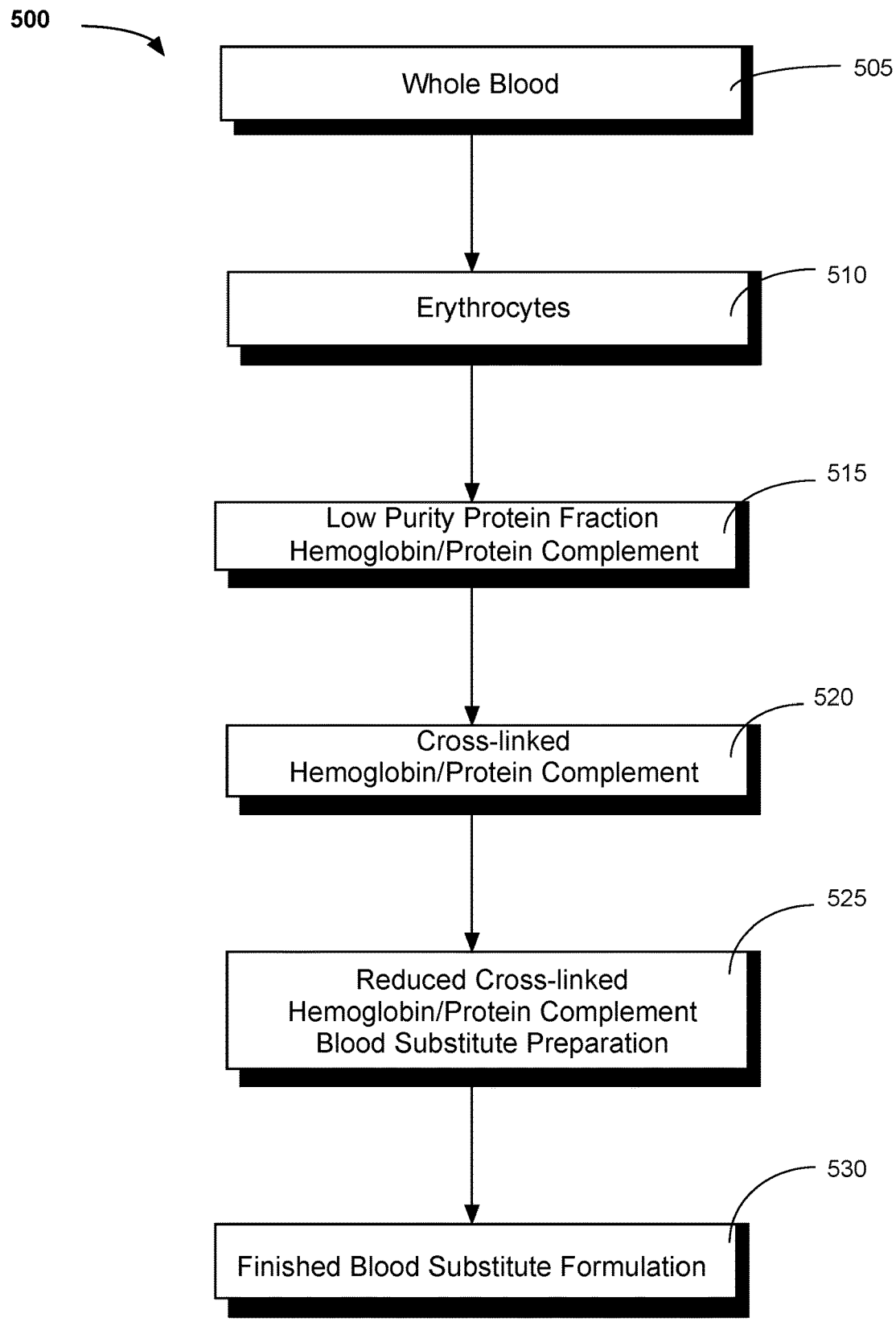

FIG. 5 depicts a schematic overview of steps of a method to a prepare blood substitute preparation and formulation in accordance with an embodiment of the present disclosure.

Figure 6:
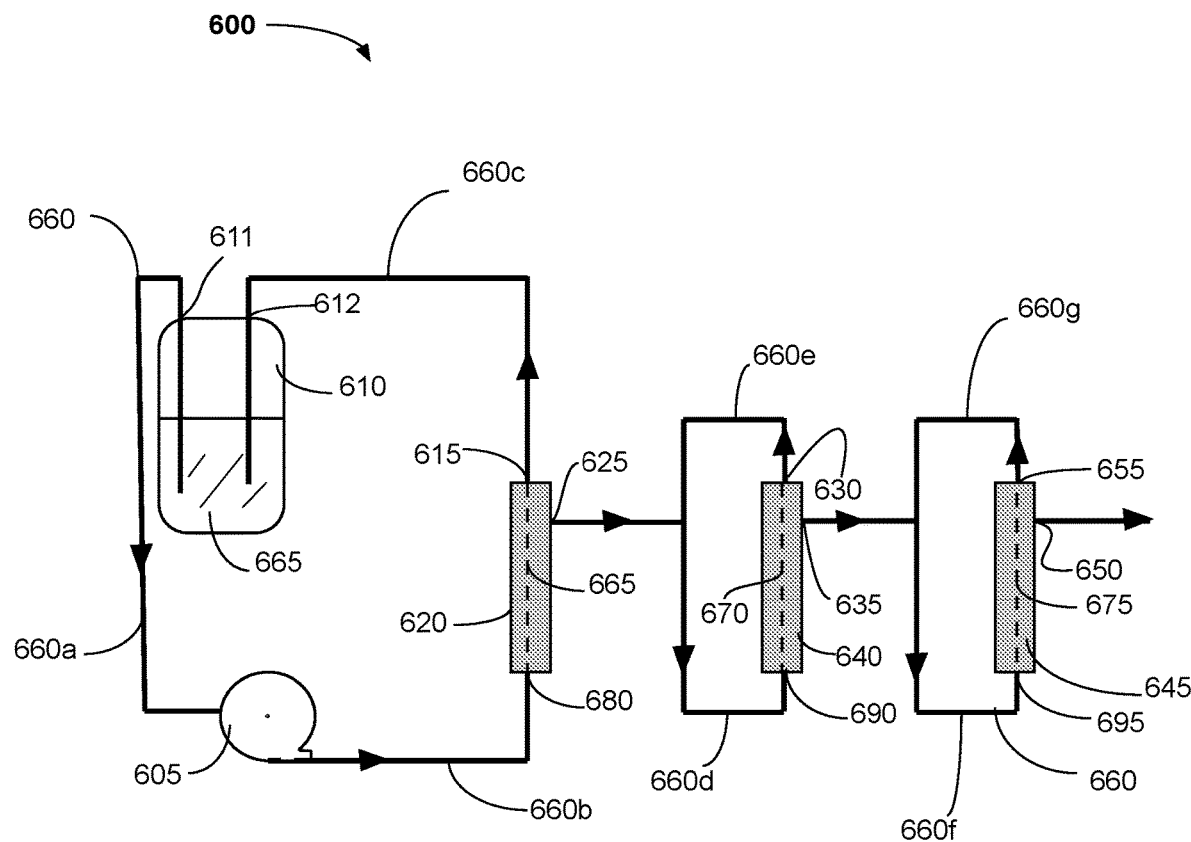

FIG. 6 depicts a schematic overview of an example assembly to perform a step of the method of the present disclosure, in particular, an assembly to prepare a low purity erythrocyte protein fraction from an erythrocyte lysate.

Figure 7:
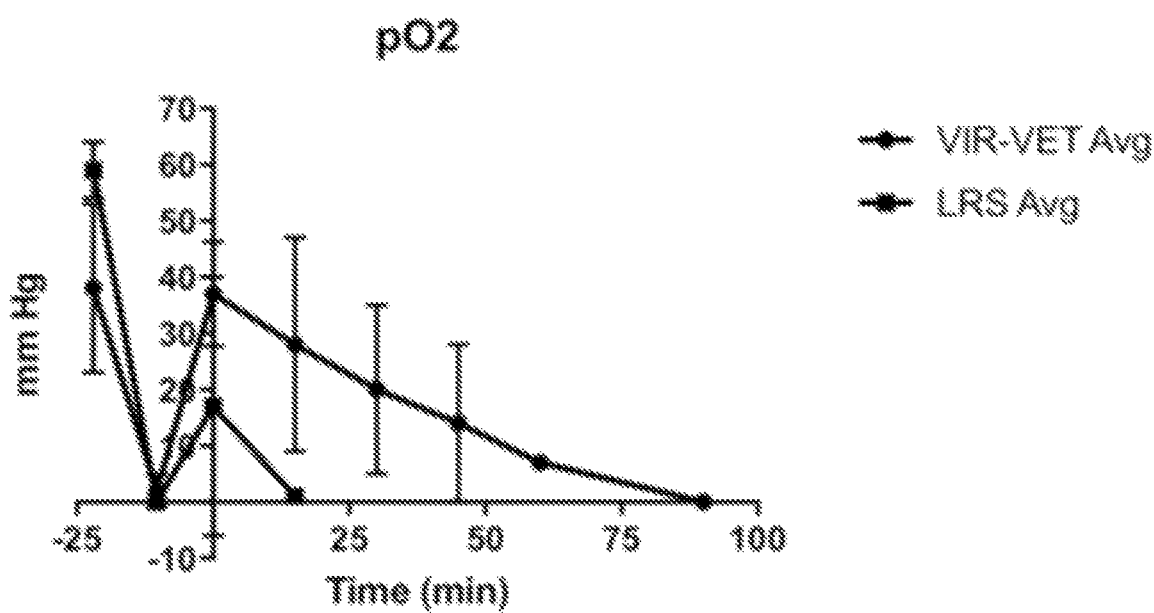

FIG. 7 depicts a graph obtained in the performance of an experiment involving the in-vivo administration of an example substitute blood preparation made according to an embodiment of the present disclosure to rats. Shown is the interstitial oxygen pressure as a function of time following injury and subsequent administration of the substitute blood preparation (denoted: VIR-VET Avg), and as Lactated Ringers Solution (denoted: LRS Avg).

Figure 8:
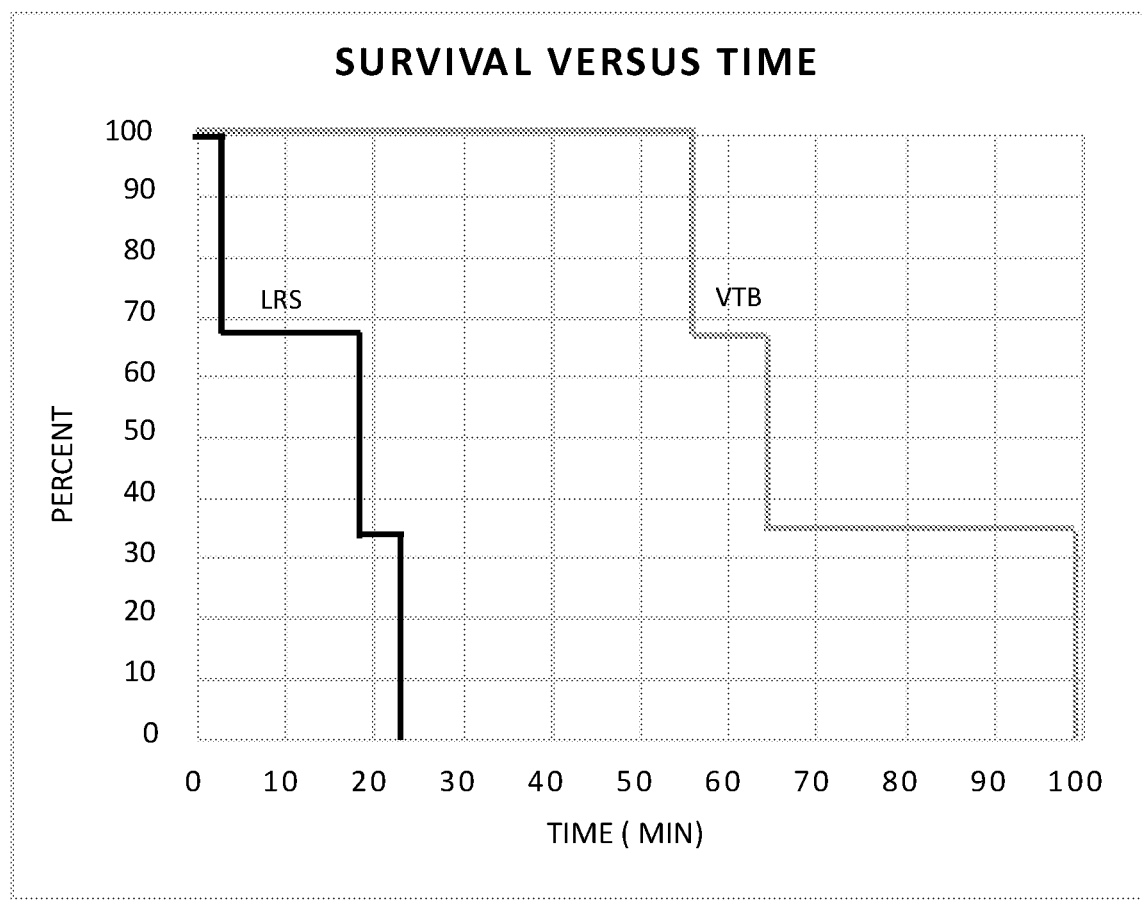

FIG. 8 depicts a graph obtained in the performance of an experiment involving the in-vivo administration of an example blood preparation according to an embodiment of the present disclosure to rats. Shown is the survival of rats as a function of time following injury and subsequent administration of the blood preparation (denoted: VTB), and Lactated Ringers Solution (denoted: LRS).

Figure 9:
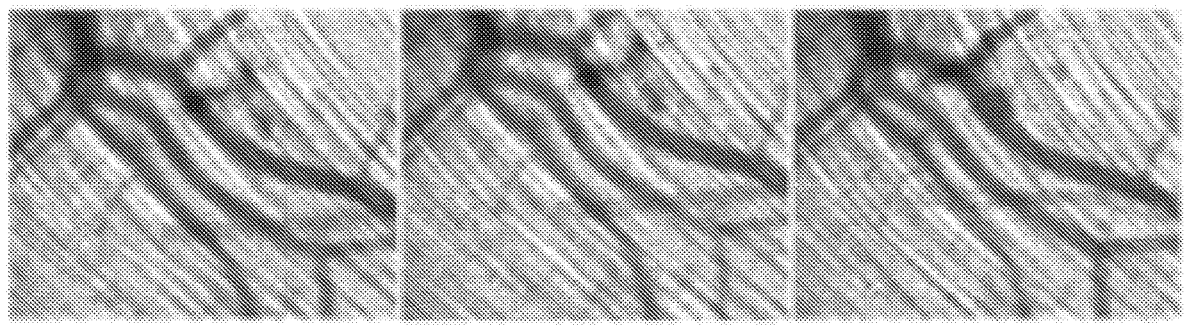

FIG. 9 depicts microscopic images obtained in the performance of an experiment involving the in-vivo administration of an example blood preparation made according to an embodiment of the present disclosure to rats. Shown are images of muscle tissue blood vessels prior to administration (denoted: baseline), at the time of administration (denoted: 10% Bolus 0 min) and 120 minutes following administration (denoted: 10% Bolus 120 min).

Figure 10A:
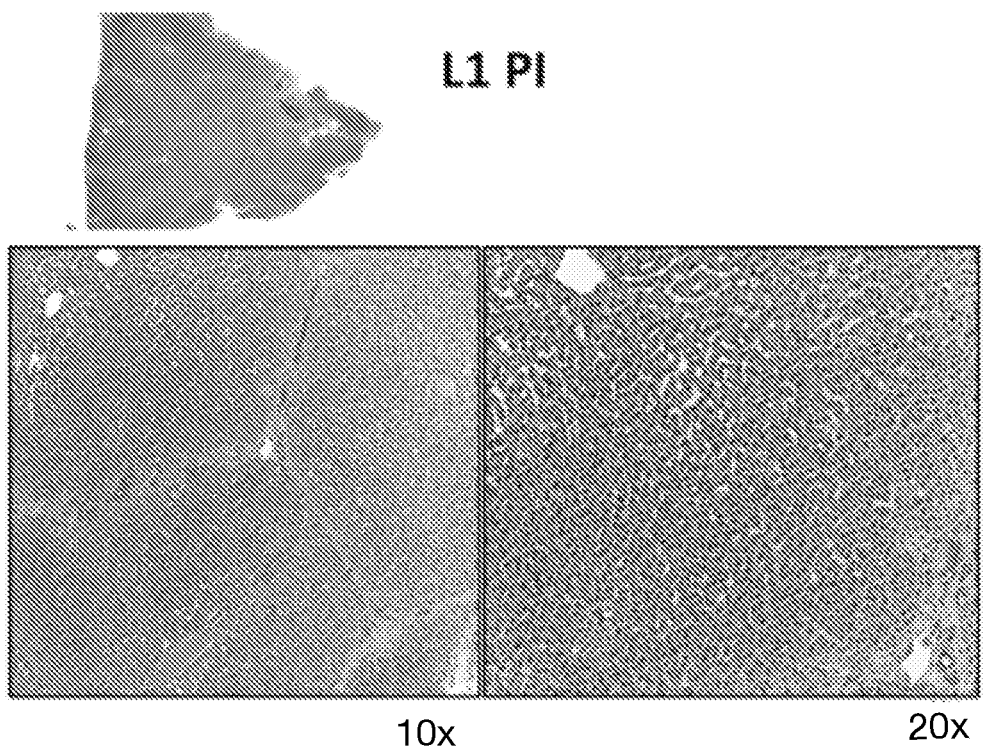
Figure 10B:
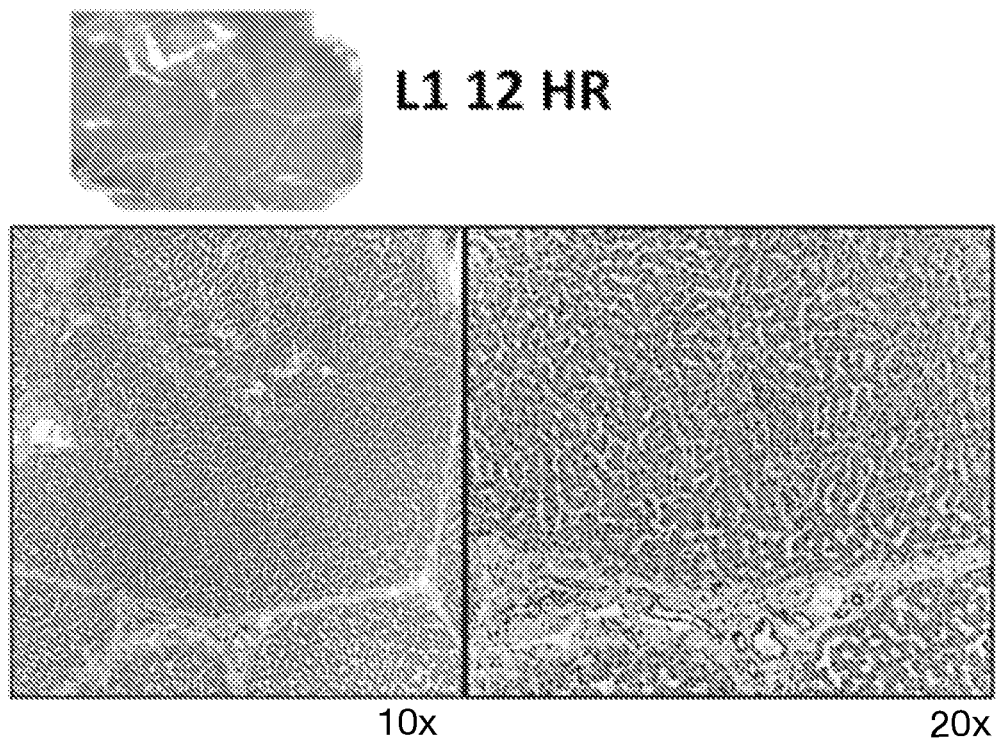

FIGS. 10A and 10B depicts microscopic images obtained in the performance of an experiment involving the ex-vivo perfusion of an example blood preparation made according to an embodiment of the present disclosure to swine livers. Images are shown at a 10× and 20× magnification prior to the initiation of perfusion (FIG. 10A), and following 12 hours of perfusion (FIG. 10B).

Figure 11:
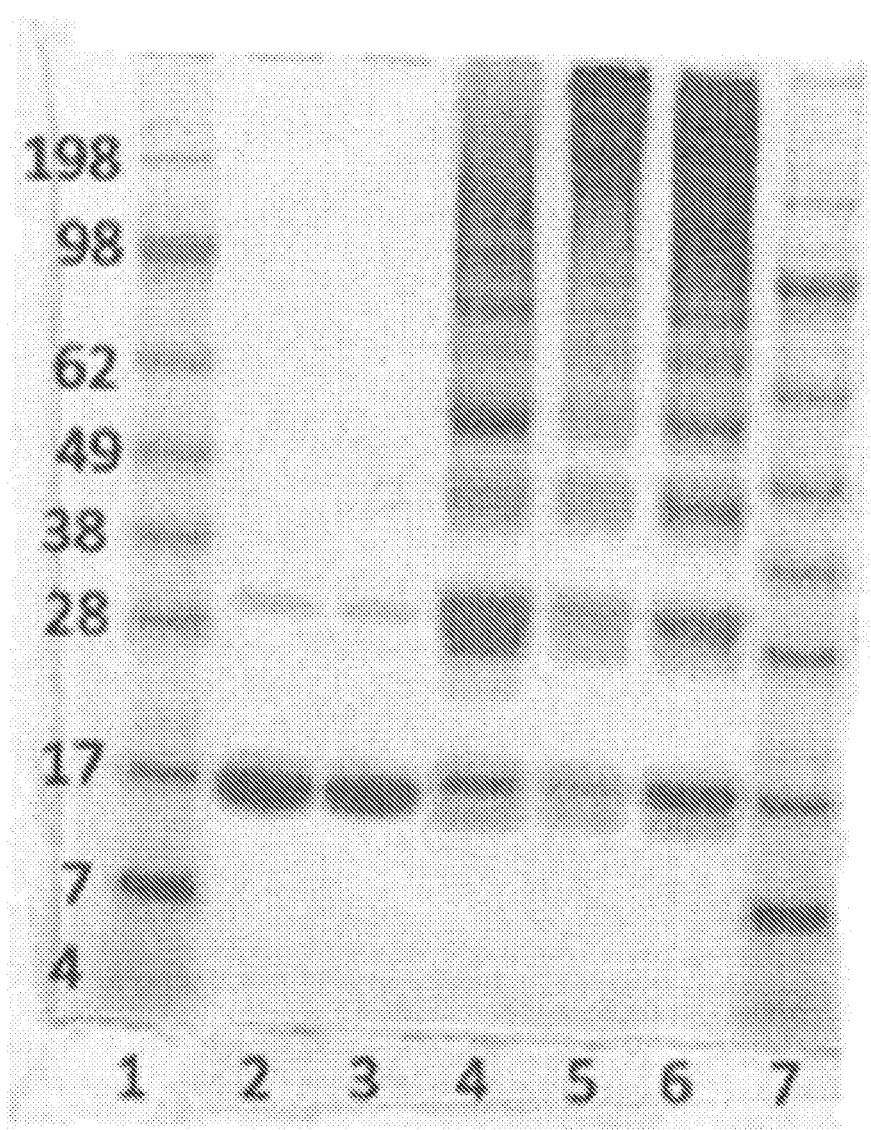

FIG. 11 depicts an SDS polyacrylamide gelelectrophoresis gel obtained in the performance of an experiment involving the separation of certain protein containing samples on the polyacrylamide gel. The protein containing samples are obtained from example preparations according to the present disclosure. Shown are: lane 1: prestained molecular size markers; lane 2: purified hemoglobin, lot number VTB-004; lane 3: purified hemoglobin, lot number VTB-009; lane 4: example 300 kDa erythrocyte protein filtrate including hemoglobin and endogenous non-hemoglobin protein complement (non-cross-linked); lane 5: example cross-linked blood substitute preparation comprising cross-linked hemoglobin and endogenous non-hemoglobin protein complement, lot number VTB009; and lane 6: example cross-linked blood substitute preparation comprising cross-linked hemoglobin and endogenous non-hemoglobin protein complement, lot number VTB007.

Figure 12A:
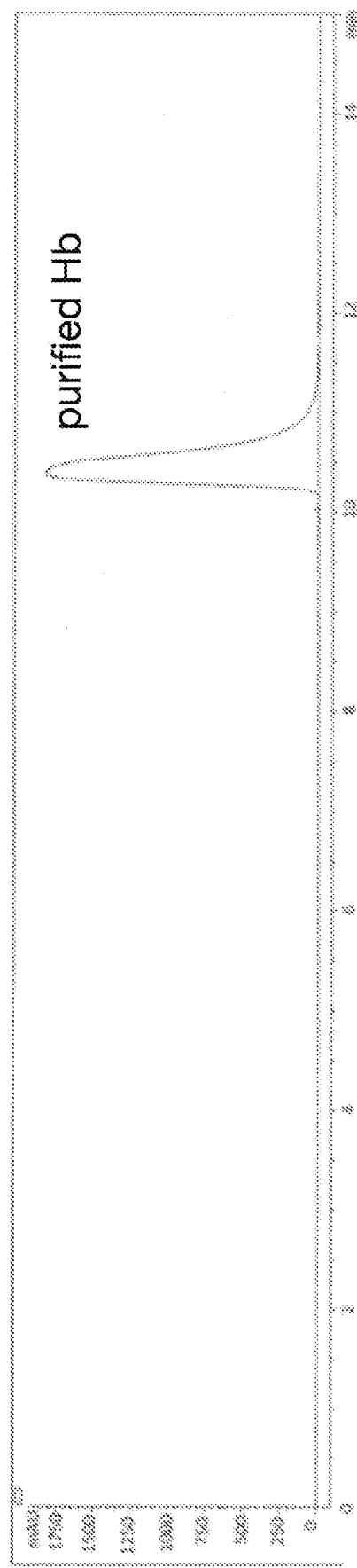
Figure 12B:
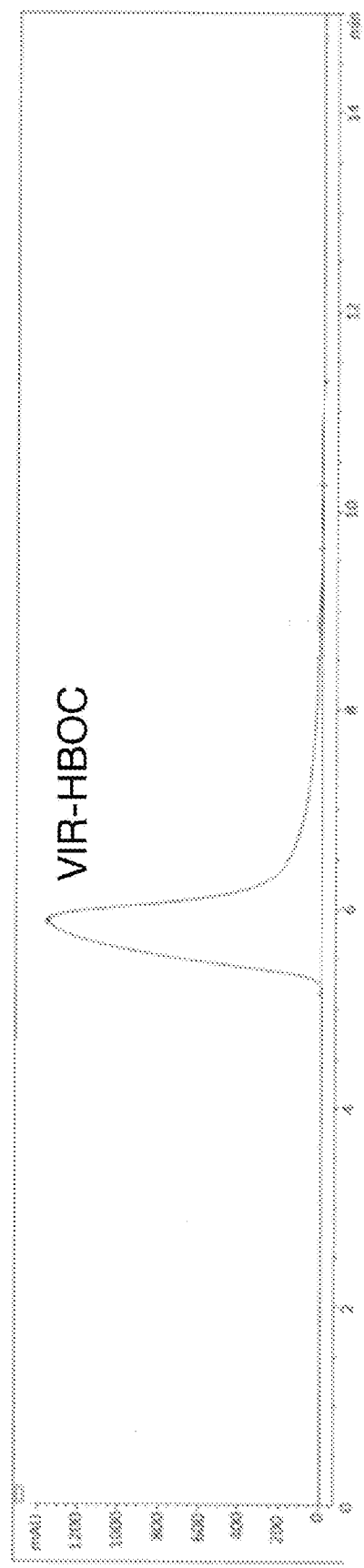
Figure 12C:
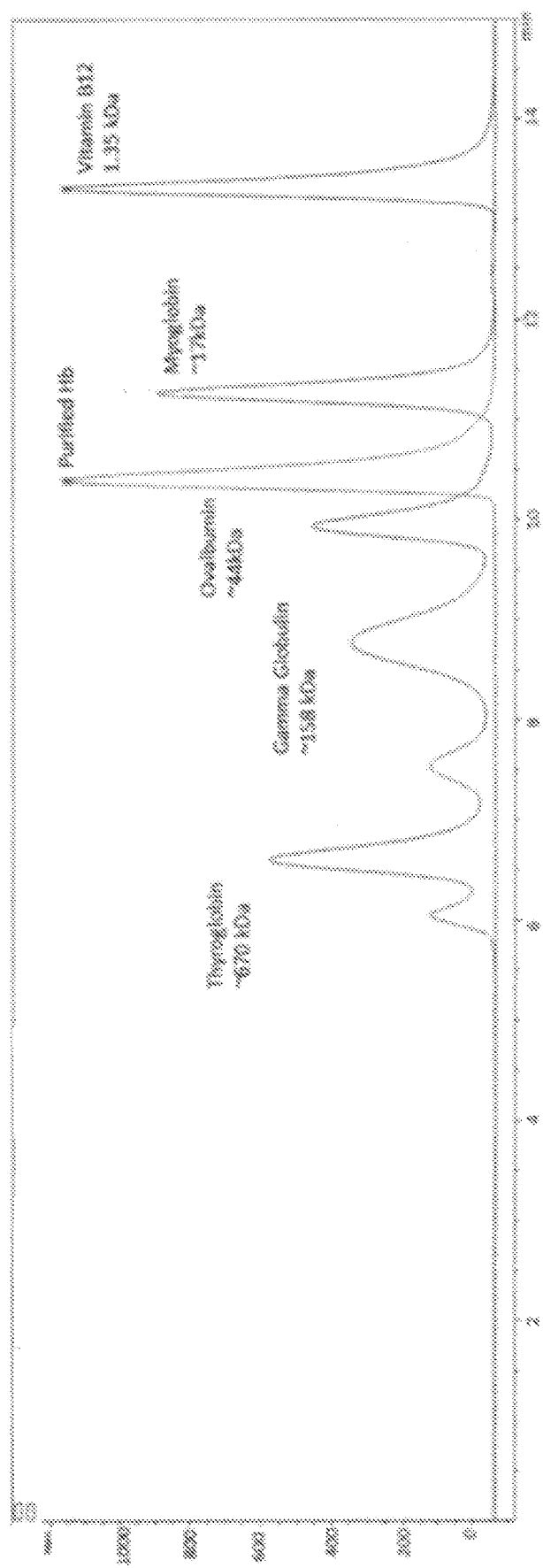

FIGS. 12A, 12B and 12C depict traces from size exclusion gel filtration chromatography experiments showing a comparison of purified hemoglobin (FIG. 12A), an example blood substitute preparation comprising cross-linked hemoglobin and endogenous non-hemoglobin protein complement (FIG. 12B), and molecular size markers (FIG. 12C).

Figure 13:
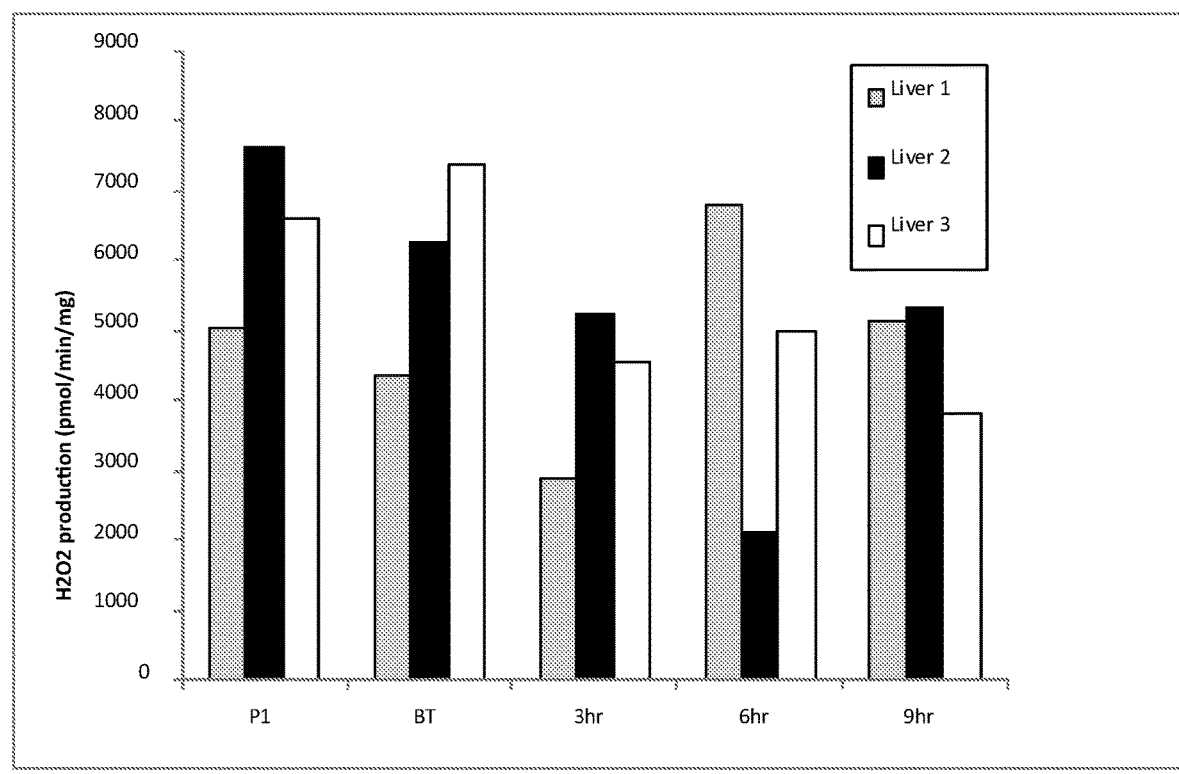

FIG. 13 depicts a bar graph obtained in the performance of an experiment involving the ex-vivo perfusion of 3 swine livers with of an example blood preparation made according to an embodiment of the present disclosure. Shown is the $H_2O_2$ production as a function of time (3 hr, 6 hr and 9 hr, following initiation of perfusion). The bars denoted by P1 represent the in-vivo level of $H_2O_2$ production of the livers prior to removal. The bars denoted by BT represent the ex-vivo level of $H_2O_2$ production upon initial perfusion.

The drawings together with the following detailed description make apparent to those skilled in the art how the disclosure may be implemented in practice.

DETAILED DESCRIPTION

Various processes, methods and compositions will be described below to provide an example of an embodiment of the claimed subject matter. No embodiment described below limits any claimed subject matter and any claimed subject matter may cover processes, methods, or compositions that differ from those described below. The claimed subject matter is not limited to any process, method, or composition having all of the features of processes, methods, or compositions described below, or to features common to multiple or processes, methods, compositions or compositions described below. It is possible that a process, method, or composition described below is not an embodiment of any claimed subject matter. Any subject matter disclosed in processes, methods, or compositions described below that is not claimed in this document may be the subject matter of another protective instrument, for example, a continuing patent application, and the applicants, inventors or owners do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either". The term "and/or" is intended to represent an inclusive or. That is "X and/or Y" is intended to mean X or Y or bot, for example. As a further example, X, Y and/or Z is intended to mean X or Y or Z or any combination thereof When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore, any range of values described herein is intended to specifically include the limiting values of the range, and any intermediate value or sub-range within the given range, and all such intermediate values and sub-ranges are individually and specifically disclosed (e.g. a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents, and patent applications referred herein are herein incorporated by reference in their entirety to the same extent as if each individual publication, patent or patent application was specifically indicated to be incorporated by reference in its entirety.

Definitions

The term "aldehyde", as used herein, refers to a chemical compound having a group represented by —CH=O.

The term "carbonic anhydrase" refers to the constituent endogenous erythrocyte protein and includes human carbonic anhydrase, including all naturally occurring variants, as well as carbonic anhydrase obtainable or obtained from other vertebrates.

The term "chemical modification", as used herein, refers to the performance of a chemical reaction using reactant molecules and resulting in the formation of product molecules, in such a manner that the reactant molecules are converted into product molecules comprising one or more newly formed covalent bonds.

The terms "covalent", "covalent linkage", and "covalent link" as may be used substantially interchangeably herein, with reference to a chemical bond, refer to a chemical bond in which electrons are shared between two atoms, and includes a reducible chemical bond which can be reduced by the addition of an additional electron.

The terms "cross-link", and "cross-linkage", as may be used interchangeably herein, refer to any chemical linkage formed between two atoms, for example, via a cross-linking molecule. Cross-links can be intramolecular crosslinks, or intermolecular crosslinks.

The term "endogenous non-hemoglobin protein complement" or, as used herein, refers to any and all of the constituent proteins in an erythrocyte preparation, other than hemoglobin.

The term "erythrocyte" or "red blood cell" or "RBC", as may be used interchangeably herein, means a non-nucleated hemoglobin containing red blood cell, generally responsible for the red color of blood.

The term "extravasation", as used herein, refers to a process of loss of molecules present in blood, such as hemoglobin, from blood vessels to extravascular tissue.

The term "ex-vivo", as used herein, with respect to the use of a blood substitute formulation, refers to the use thereof to transport and deliver oxygen to an organ, tissue or cells outside a living subject.

By "formulating the blood substitute preparation to form a finished blood substitute formulation" it is meant that the blood substitute preparation is contacted (e.g. mixed) with at least one other ingredient, including, but not limited to, a diluent, excipient or carrier, and mixed, homogenized or prepared until a finished blood substitute formulation is formed.

The term "finished blood substitute formulation", as used herein, refers to a fully formulated blood substitute formulation comprising a blood substitute preparation suitable for ex-vivo or in-vivo use.

Figure 1A:
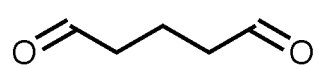
FIGS. 1A and 1B depict the chemical formula of a monomeric form of glutaraldehyde and a polymeric form of glutaraldehyde, respectively.
Figure 1B:
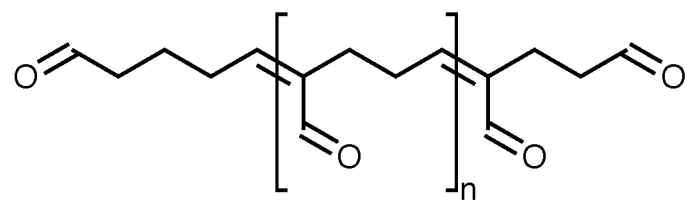

The term "glutaraldehyde", as used herein, refers to the chemical compounds shown in FIG. 1A and FIG. 1B, and include the monomeric form of glutaraldehyde, as shown in FIG. 1A, and polymeric forms of glutaraldehyde as shown in FIG. 1B, wherein in FIG. 1B, n is a positive integer, and wherein n preferably, is 1, 2, 3, 4, 5, 6, 7, 8, 9, 10, 11, 12, 13, 14 or 15.

The term "hemoglobin" and "hemoglobin molecule", as used interchangeably herein, refers to the protein contained within erythrocytes that transports oxygen in living organisms. Each molecule of hemoglobin has 4 subunits, 2 α-chains and 2 β-chains, which are arranged in a tetrameric structure. Each subunit also contains one heme group, which is the iron-containing center that binds oxygen. Thus, each hemoglobin molecule can bind 4 oxygen molecules. As used herein, the term by itself refers to native hemoglobin, including naturally occurring variants thereof, and further includes hemoglobin obtainable from any living organism, including, without limitation, vertebrate hemoglobin, including, without limitation, mammalian and avian hemoglobin, e.g. human hemoglobin, bovine hemoglobin, ovine hemoglobin, and porcine hemoglobin.

The terms "intermolecular cross-link" and "intermolecular cross-linkage", as may be used interchangeably herein, refer to a non-natively present cross-link between two molecules, for example, between two hemoglobin molecules, or between a hemoglobin molecule and a protein present in an endogenous non-hemoglobin protein complement.

The terms "intramolecular cross-link" or "intramolecular cross-linkage", as may be used interchangeably herein, refer to a non-natively present cross-link formed within a molecule, for example, between two amino acids in a protein present in the endogenous non-hemoglobin protein complement, between two amino acids within the same α-chain of a hemoglobin molecule, or between an amino acid of an α-chain and an amino acid of a β-chain of the same hemoglobin molecule.

The term "in-vivo", as used herein, with respect to the use of a blood substitute formulation, refers to the administration thereof to a subject, i.e. a human or an animal.

The term "polyaldehyde", as used herein, refers to a chemical compound having at least two aldehyde groups and includes, but is not limited to, glutaraldehydes.

The term "Schiff base", as used herein, refers to any compound containing an azomethine cross-linkage —CH=N—, also known as an imine linkage, having a carbon atom directly attached at either end. The azomethine cross-linkage can have attached thereto both aliphatic and aromatic substituents. The term is also meant to include similar compounds wherein the hydrogen of the azomethine linkage is replaced with a carbon atom, e.g.:

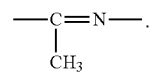

The term "superoxide dismutase" refers to the constituent endogenous erythrocyte protein and includes human superoxide dismutase, including all naturally occurring variants, as well as superoxide dismutase obtainable or obtained from other vertebrates.

"Low purity", as used herein, with respect to an erythrocyte protein fraction, refers to an erythrocyte protein fraction wherein the endogenous non-hemoglobin protein complement comprises from at least about 0.2% (mole/mole) up to about 20% (mole/mole), from at least about 0.3% (mole/mole) up to about 20% (mole/mole), from at least about 0.4% (mole/mole) up to about 20% (mole/mole), from at least about 0.5% (mole/mole) up to about 20% (mole/mole), from at least about 1% (mole/mole) up to about 20% (mole/mole), from at least about 2% (mole/mole) up to about 20% (mole/mole), from at least about 3% (mole/mole) up to about 20% (mole/mole), from at least about 4% (mole/mole) up to about 20% (mole/mole), from at least about 5% (mole/mole) up to about 20% (mole/mole), from at least about 6% (mole/mole) up to about 20% (mole/mole), from at least about 7% (mole/mole) up to about 20% (mole/mole), from at least about 8% (mole/mole) up to about 20% (mole/mole), from at least about 9% (mole/mole) up to about 20% (mole/mole), from at least about 10% (mole/mole) up to about 20% (mole/mole), or from at least about 15% (mole/mole) up to about 20% (mole/mole) of the total protein present in the erythrocyte protein fraction.

"Substantially pure", as used herein, herein describe an entity, e.g. a cell or chemical compound, which has been separated from constituents that naturally accompany it. Typically, an entity is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the entity of interest. With reference to an erythrocyte preparation, the term further refers to the separation from of non-erythrocyte blood cells, e.g. leukocytes and thrombocytes including a preparation comprising no more than 5%, 4%, 3%, 2% or 1% of non-erythrocyte blood cells. Purity can be measured by any appropriate method, e.g., in the case of proteins, by chromatography, gel electrophoresis or HPLC analysis, and in the case of erythrocytes, flow cytometry.

General Implementation

In overview it has surprisingly been realized, that lower purity hemoglobin preparations can be used to prepare blood substitutes. The preparations of the present disclosure can be manufactured by obtaining erythrocytes and preparing a low purity protein preparation from the erythrocytes. The low purity protein preparation is prepared to contain, besides hemoglobin, substantial quantities of endogenous non-hemoglobin protein complement. The techniques of the present disclosure represent a substantially less complex alternative to known blood substitute manufacturing techniques by avoiding complex purification methodologies to obtain highly pure hemoglobin. Furthermore in accordance with the teachings of the present disclosure it is possible to avoid the use of borohydride ($BH_4^-$). Thus, manufacturing operations do not need to take into consideration the precautionary measures ordinarily required when borohydride is used.

In an embodiment, the low purity protein preparation can be contacted with a reactant capable of chemically modifying proteins in the preparation to obtain cross-linked proteins. The cross-linked proteins can comprise intermolecular cross-linkages between the hemoglobin protein molecules and intermolecular cross-linkages between the hemoglobin protein molecules and the endogenous non-hemoglobin protein complement. Substantial quantities of the hemoglobin protein molecules in the erythrocyte protein fraction can be cross-linked, so that, in an embodiment, the average molecular mass of cross-linked proteins in the preparation can be, for example, at least about 300 kDa. The thus obtained novel blood substitute preparations can be used to prepare finished blood formulations.

The blood substitute preparations of the present disclosure can provide tissue oxygenation and thereby mediate tissue survival. The preparations of the present disclosure can further be said to be characterized by exhibiting a low colloid osmotic pressure (COP) and a high viscosity. When formulations comprising the preparations of the present disclosure are administered to a subject in need thereof, these attributes are believed to result in limited or no narrowing of the blood vessels, a physiological process also referred to as vasoconstriction, and/or limited or no leakage of hemoglobin from the blood vessels, a physiological process also referred to as extravasation. Furthermore, the formation of reactive oxygen species in the preparations of the present disclosure can be said to be limited, thus minimizing damage to the endothelial glycocalyx of blood vessels. A yet further beneficial characteristic the blood substitute preparations of the present disclosure have realized, is the presence of limited quantities of methemoglobin in the preparations. Thus, the methods of the present disclosure provide a safe, easy and economical means to manufacture novel blood substitute preparations which can be used to prepare finished blood substitute formulations for in-vivo use, for example, during surgical procedures, and for ex-vivo use, for example, in order to preserve tissues and organs for transplantation.

In what follows selected embodiments are described with reference to the drawings for illustration purposes. Accordingly, the present disclosure provides, in one embodiment, a method of preparing a blood substitute preparation comprising hemoglobin, the method comprising:

(i) isolating erythrocytes from blood;
(ii) isolating a low purity erythrocyte protein fraction comprising hemoglobin protein molecules and endogenous non-hemoglobin protein complement from the erythrocytes, the low purity erythrocyte protein fraction comprising from at least about 0.2% (mole/mole) up to about 20% (mole/mole) endogenous non-hemoglobin protein complement; and
(iii) contacting the low purity erythrocyte protein fraction with a reactant capable of chemically modifying the proteins in the protein fraction, the reactant thereby mediating the formation of cross-linked proteins comprising intermolecular cross-linkages between the hemoglobin protein molecules, and intermolecular cross-linkages between the hemoglobin protein molecules and the endogenous non-hemoglobin protein complement, to thereby form a blood substitute preparation.

In one embodiment, at least about 90% (mole/mole) of the hemoglobin proteins in the erythrocyte protein fraction can be cross-linked, so that the average molecular mass of cross-linked proteins is at least about 300 kDa.

In one embodiment, the endogenous non-hemoglobin protein complement can comprise carbonic anhydrase, wherein the carbonic anhydrase comprises from at least about 0.2% (mole/mole) up to 15% (mole/mole) of the endogenous non-hemoglobin protein complement.

In one aspect, initially a low purity erythrocyte protein fraction comprising hemoglobin protein and endogenous non-hemoglobin protein complement can be obtained. In what follows the preparation of a low purity erythrocyte protein fraction is described briefly and in general terms.

Selected embodiments for obtaining a low purity erythrocyte protein fraction will hereinafter further described in further detail with reference to FIG. 5 and FIG. 6.

In accordance herewith, a low purity erythrocyte protein fraction can be isolated from an erythrocyte preparation, preferably a substantially pure erythrocyte preparation, prepared from blood, including without limitation, human blood, preferably free from viral disease contaminants, using the methodologies hereinafter described, or any other suitable methodology for the preparation of erythrocytes. A low purity erythrocyte protein fraction can be obtained from the erythrocyte preparation by lysing the erythrocytes within the preparation, and thereafter separating a protein fraction comprising hemoglobin and endogenous non-hemoglobin protein complement from the lysate using, for example, filtering methodologies, as hereinafter described, or any suitable protein fractionation technique. In accordance herewith, the obtained low purity erythrocyte protein fraction is a protein fraction comprising from at least about 0.2% (mole/mole) up to about 20% (mole/mole), from at least about 0.3% (mole/mole) up to about 20% (mole/mole), from at least about 0.4% (mole/mole) up to about 20% (mole/mole), from at least about 0.5% (mole/mole) up to about 20% (mole/mole), from at least about 1% (mole/mole) up to about 20% (mole/mole), from at least about 2% (mole/mole) up to about 20% (mole/mole), from at least about 3% (mole/mole) up to about 20% (mole/mole), from at least about 4% (mole/mole) up to about 20% (mole/mole), from at least about 5% (mole/mole) up to about 20% (mole/mole), from at least about 6% (mole/mole) up to about 20% (mole/mole), from at least about 7% (mole/mole) up to about 20% (mole/mole), from at least about 8% (mole/mole) up to about 20% (mole/mole), from at least about 9% (mole/mole) up to about 20% (mole/mole), from at least about 10% (mole/mole) up to about 20% (mole/mole), from at least about 15% (mole/mole) up to about 20% (mole/mole) endogenous non-hemoglobin protein complement, with the balance comprising hemoglobin.

In one embodiment, the endogenous non-hemoglobin protein complement can include the following endogenous non-hemoglobin protein complement proteins: carbonic anhydrase and/or superoxide dismutase.

In one embodiment, the endogenous non-hemoglobin protein complement can comprise from about 0.2% (mole/mole) to about 15% (mole/mole) carbonic anhydrase.

In one aspect, the low purity erythrocyte protein fraction can be contacted with a reactant capable of chemically modifying the proteins in the erythrocyte protein fraction to thereby mediate the formation of cross-linked proteins.

In one embodiment, the reactant can mediate the formation of cross-linked proteins comprising intermolecular cross-linkages between the hemoglobin protein molecules, and intermolecular cross-linkages between the hemoglobin protein molecules and the endogenous non-hemoglobin protein complement.

In one embodiment, the reactant can mediate the formation of cross-linked proteins so that the formed protein molecules have a molecular mass sufficiently large to prevent extravasation of hemoglobin upon administration of the blood substitute preparation to a subject in need thereof.

In one embodiment, the reactant can mediate the formation of cross-linked proteins so that the formed proteins have an average molecular mass of about or at least about 300 kDa, at about or least about 400 kDa, about or at least about 500 kDa, about or at least about 600 kDa, about or at least about 700 kDa, about or at least about 800 kDa, about or at least about 900 kDa, about or at least about 1,000 kDa, about or at least about 1,100 kDa.

In one embodiment, the reactant can mediate the formation of cross-linked proteins so that all or substantially all of the formed protein molecules have a molecular mass of about or at least about 120 kDa, about or at least about 180 kDa, about or at least about 250 kDa, about or at least about 300 kDa, about or at least about 400 kDa, about or at least about 500 kDa, about or at least about 600 kDa, about or at least about 700 kDa, about or at least about 800 kDa, about or at least about 900 kDa, about or at least about 1,000 kDa, or about or at least about 1,100 kDa.

In one embodiment, the reactant can mediate the formation of cross-linked proteins so that at least about 90% (mole/mole), at least about 95% (mole/mole), at least about 96% (mole/mole), at least about 97% (mole/mole), at least about 98% (mole/mole), or at least about 99% (mole/mole) of the formed protein molecules have a molecular mass of about or at least about 120 kDa, about or at least about 180 kDa, about or at least about 250 kDa, about or at least about 300 kDa, about or at least about 400 kDa, about or at least about 500 kDa, about or at least about 600 kDa, about or at least about 700 kDa, about or at least about 800 kDa, about or at least about 900 kDa, about or at least about 1,000 kDa, or at least about 1,100 kDa.

In one embodiment, the reactant that can mediate the formation of cross-linked proteins can be a polyaldehyde. The polyaldehyde can be reacted under reaction conditions permitting a chemical reaction between aldehyde groups of the polyaldehyde and amino groups of the proteins to form a plurality of covalent intermolecular cross-linkages between the hemoglobin protein molecules, and between the hemoglobin protein molecules and the endogenous non-hemoglobin protein complement. In accordance herewith, any polyaldehyde may be used to cross-link the endogenous non-hemoglobin protein complement to hemoglobin present in the low purity erythrocyte protein fraction. The concentration of the polyaldehyde can vary, for example, a final concentration from about 0.15 g/l to about 20 g/l of polyaldehyde may be used.

In one embodiment, the polyaldehyde can be glutaraldehyde, which can be used in a final concentration of from about 0.15 g/l to about 2 g/l. In preferred embodiments, glutaraldehyde is used in a final concentration of about 1.2 g/l.

In one embodiment, the polyaldehyde can be succinaldehyde, which can be used in a final concentration of from about 0.15 g/l to about 1.7 g/l. In preferred embodiments, glutaraldehyde is used in a concentration of about 1.0 g/l.

In one embodiment, the reactant that can mediate the formation of cross-linked proteins can be o-raffinose.

In one embodiment, the reactant that can mediate the formation of cross-linked proteins can be bis (3,5 dibromosalicyl) adipate.

The concentration of the reactant can vary but should be should be sufficient to form a plurality of covalent intermolecular cross-linkages between the hemoglobin protein molecules, and between the hemoglobin protein molecules and the endogenous non-hemoglobin protein complement. As noted, where polyaldehydes are used as a reactant, the concentration of polyaldehyde can be between about 0.15 g/l to about 20 g/l. The concentration of the reactant may be optimized or adjusted, for example by preparing a plurality of erythrocyte protein samples; including in each sample a different concentration of reactant; and upon completion of the chemical modification reaction determining the average molecular mass of the cross-linked protein and/or the fraction of cross-linked proteins. Then, a concentration of reactant can be selected that provides cross-linked protein molecules having a certain average molecular mass, for example, at least 300 kDa. Other reaction parameters, such as temperature or pH, may similarly be determined. There may be variation in optimal conditions, including the concentration of reactant, depending on the use of the blood substitute preparation, for example for in-vivo or ex-vivo use.

As hereinbefore noted in one embodiment, glutaraldehyde can be used as a reactant. In what follows, by way of example, the use of glutaraldehyde (see: FIG. 1A-1B) as a reactant in accordance with the present disclosure is further illustrated.

Figure 2:
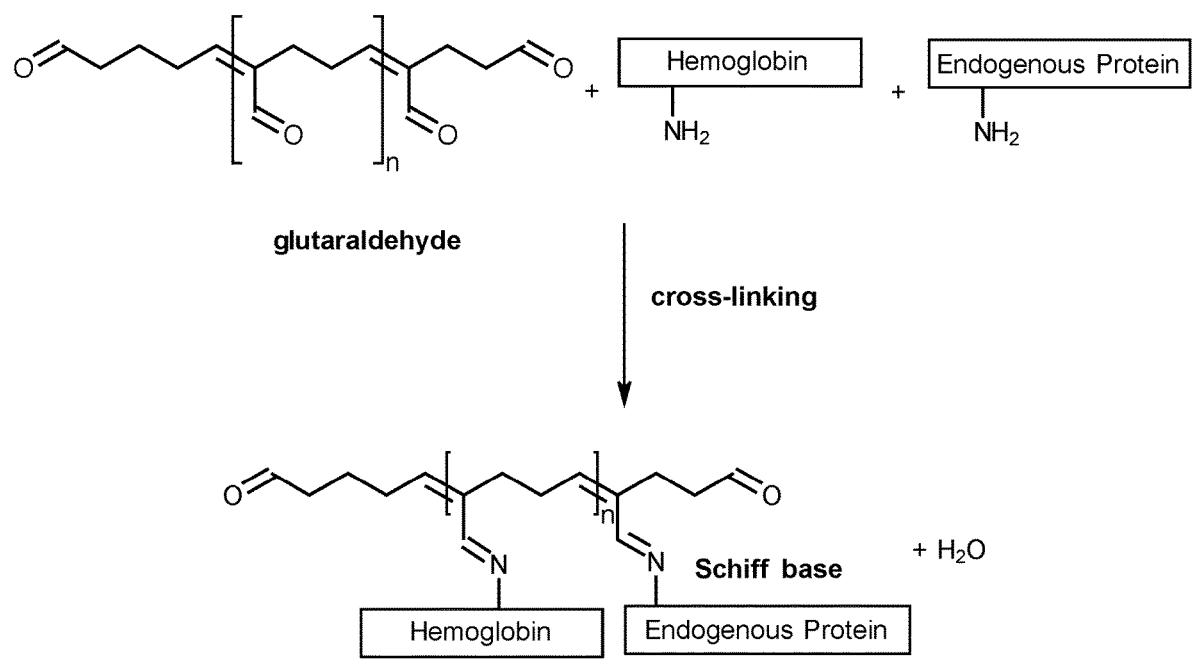
FIG. 2 depicts an example chemical reaction for cross-linking a hemoglobin to a protein present in an endogenous non-hemoglobin protein complement using a glutaraldehyde thereby forming a Schiff base.

Referring now to FIG. 2, shown therein is representation of an example chemical reaction between a polyglutaraldehyde and a hemoglobin protein and a constituent endogenous non-hemoglobin protein complement protein. It is noted that for ease of illustration, only one amino ($NH_2$) group is depicted in each protein. Both proteins, however, comprise a plurality of amino groups, including the amino groups provided by lysine, arginine, asparagine and glutamine, as well as the N-terminal amino groups, all of which can participate in the depicted reaction. A chemical reaction between a first and second aldehyde group within the polyglutaraldehyde molecule with a first amino group within a hemoglobin molecule and a second amino group of a constituent endogenous non-hemoglobin protein complement protein, results in intermolecular cross-linking between the hemoglobin and constituent endogenous non-hemoglobin protein complement proteins, with the reaction forming two covalent cross-linkages and a cross-linked-protein. As shown in FIG. 2, in one embodiment, the cross-linkages can be reducible Schiff bases. The reaction may be conducted under a variety of conditions, including, for example, in phosphate buffers having a slightly basic pH, e.g. pH 7.5-8.5 or HEPES buffers, preferably at temperatures above room temperature, for example at 37° C.

It is noted that contacting of the erythrocyte protein fraction with the reactant capable of chemically modifying the proteins in the protein fraction can result in the formation of intermolecular cross cross-linkages between various protein molecules.

In one embodiment, covalently intermolecularly cross-linked hemoglobin protein molecules can be formed, wherein a covalently intermolecularly cross-linked hemoglobin protein molecule can comprise one or more covalent intermolecular cross-linkages.

In one embodiment, covalently intermolecularly cross-linked endogenous non-hemoglobin protein complement molecules can be formed, wherein a covalently intermolecularly cross-linked endogenous non-hemoglobin protein complement molecules can comprise one or more covalent intermolecular cross-linkages.

In one embodiment, covalently intermolecularly cross-linked hemoglobin protein molecules and covalently intermolecularly cross-linked endogenous non-hemoglobin protein complement molecules can be formed, wherein a covalently intermolecularly cross-linked protein hemoglobin molecule can comprise one or more intermolecular cross-linkages, and wherein a covalently intermolecularly cross-linked endogenous non-hemoglobin protein complement molecule can comprise one or more intermolecular cross-linkages.

In one embodiment, hemoglobin protein molecules covalently intermolecularly cross-linked to endogenous non-hemoglobin protein complement molecules can be formed, wherein a hemoglobin protein molecule cross-linked to an endogenous non-hemoglobin protein complement molecule can comprise one or more covalent intermolecular linkages.

In one embodiment, covalently intermolecularly cross-linked hemoglobin protein molecules, covalently intermolecularly cross-linked endogenous non-hemoglobin protein complement molecules and hemoglobin protein molecules covalently intermolecularly cross-linked to endogenous non-hemoglobin protein complement molecules can be formed, wherein a covalently intermolecularly cross-linked hemoglobin molecule can comprise one or more intermolecular cross-linkages, wherein a covalently intermolecularly cross-linked endogenous non-hemoglobin protein complement molecule can comprise one or more covalent intermolecular cross-linkages, and wherein a hemoglobin molecule cross-linked to an endogenous non-hemoglobin protein complement molecule can comprise one or more covalent intermolecular linkages.

Furthermore, it is noted that in one embodiment, covalent intramolecular cross-linkages can be formed.

Reactants capable of forming intramolecular protein cross-linkages that can be used in accordance with the present disclosure are a polyaldehyde, such as glutaraldehyde, 2-nor-2-formylpyroxidal 5'-phosphate (NFPLP), to thereby intra-molecularly crosslink hemoglobin β-chains, or diaspirin to thereby intra-molecularly cross-link hemoglobin α-chains via bis (3,5-dibromosalicyl) fumarate.

In one embodiment, covalently intramolecularly cross-linked hemoglobin molecules can be formed, wherein a covalently intramolecularly cross-linked hemoglobin molecule can comprise one or more covalent intramolecular cross-linkages.

In one embodiment, covalently intramolecularly cross-linked endogenous non-hemoglobin protein complement molecules can be formed, wherein covalently intramolecularly cross-linked endogenous non-hemoglobin protein complement molecules can comprise one or more covalent intramolecular cross-linkages.

In one embodiment, covalently intramolecularly cross-linked hemoglobin molecules and covalently intramolecularly cross-linked endogenous non-hemoglobin protein complement molecules can be formed, wherein a covalently intramolecularly cross-linked hemoglobin molecule can comprise one or more covalent intramolecular cross-linkages, and wherein a covalently intramolecularly cross-linked endogenous non-hemoglobin protein complement molecule can comprise one or more covalent intramolecular cross-linkages.

In one embodiment, covalently intramolecularly cross-linked hemoglobin molecules, covalently intermolecularly cross-linked hemoglobin molecules, and hemoglobin molecules covalently intermolecularly cross-linked to endogenous non-hemoglobin protein complement molecules can be formed, wherein a covalently intramolecularly cross-linked hemoglobin molecule can comprise one or more covalent intramolecular cross-linkages, wherein a covalently intermolecularly cross-linked hemoglobin molecule can comprise one or more covalent intermolecular cross-linkages, and wherein a hemoglobin molecule cross-linked to an endogenous non-hemoglobin protein complement molecule can comprise one or more covalent intermolecular linkages.

In further embodiments, conjugating agents can be used to form hybrid conjugated proteins.

In one embodiment, the conjugating agents can be used before reaction with the chemical modification agent to form intermolecular cross-linkages.

In one embodiment, the conjugating agents can be used after reaction with the chemical modification agent to form intermolecular cross-linkages.

Examples of conjugating agents that can be used in accordance herewith include pyridoxal, a polyethylene glycol (PEG), including maleimide PEG, succinimidyl carbonate $PEG_{5000}$, or methoxy $PEG_{5000}$. Upon reaction with a conjugating agent hybrid conjugated proteins, such as PEGylated hemoglobin can be formed.

As hereinbefore noted, the size of the intermolecularly cross-linked proteins can vary and, in accordance herewith, preparations can be obtained comprising a cross-linked protein consisting of, for example, 2, 3, 4, 5, 6, 7, 8, 9, 10, 15, 20, 30, 40, 50 or 100 individual proteins (i.e. individual hemoglobins and/or endogenous non-hemoglobin protein complement proteins), or mixtures comprising a plurality of cross-linked proteins varying in size within the foregoing range. In one embodiment, the molecular weight can range from 120 kDa to about 20,000 kDa. The relative amount of hemoglobin in a cross-linked protein may vary. In one embodiment, at least 50%, 60%, 70%, 80%, or least 90% (mole/mole) of the individual proteins within a cross-linked protein can be a hemoglobin.

Furthermore, the amount of hemoglobin molecules present in the erythrocyte fraction participating in cross-linkage can vary. In some embodiments, all, or substantially all, hemoglobin molecules present in the erythrocyte fraction are cross-linked to other hemoglobin or to endogenous non-hemoglobin protein molecules via a covalent cross-linkage upon completion of the cross-linking reaction. In one embodiment, at least about 90% (mole/mole), at least about 95% (mole/mole), at least about 96% (mole/mole), at least about 97% (mole/mole), at least about 98% (mole/mole), at least about 99% (mole/mole) of hemoglobin protein molecules present in the erythrocyte fraction can be cross-linked via cross-linkages to another hemoglobin, or to an endogenous non-hemoglobin protein molecule upon completion of the cross-linking reaction.

Furthermore, the amount of intermolecular cross-linkages that is formed can vary. It will be clear, that cross linked hemoglobin molecules comprise at least one cross-linkage. In other embodiments, all, or substantially all cross-linked hemoglobin protein molecules present in the blood substitute preparation can comprise, at least two, at least three, at least four, or at least five cross-linkages.

In one embodiment, upon cross-linking, the molecular mass of all or substantially all of the formed cross-linked molecules can be at about or least about 120 kDa, about or at least about 180 kDa, about or at least about 250 kDa, about or at least about 300 kDa, about or at least about 400 kDa, about or at least about 500 kDa, about or at least about 600 kDa, about or at least about 700 kDa, about or at least about 800 kDa, about or at least about 900 kDa, about or at least about 1,000 kDa, or about or at least about 1,100 kDa.

In one embodiment, upon cross-linking at least about 90% (mole/mole), at least about 95% (mole/mole), at least about 96% (mole/mole), at least about 97% (mole/mole), at least about 98% (mole/mole), or at least about 99% (mole/mole) of the formed cross-linked molecules can have a molecular mass of about or at least about 120 kDa, about or at least about 180 kDa, about or at least about 250 kDa, about or at least about 300 kDa, about or at least about 400 kDa, about or at least about 500 kDa, about or at least about 600 kDa, about or at least about 700 kDa, about or at least about 800 kDa, about or at least about 900 kDa, about or at least about 1,000 kDa, or about or at least about 1,100 kDa.

In one embodiment, the formed cross-linked molecules can have an average molecular mass of about or at least about 300 kDa, about or at least about 400 kDa, about or at least about 500 kDa, about or at least about 600 kDa, about or at least about 700 kDa, about or at least about 800 kDa, about or at least about 900 kDa, about or at least about 1,000 kDa, or about or at least about 1,100 kDa.

Thus, it will be clear from the foregoing that a variety of cross-linked proteins and mixtures of such cross-linked proteins may be prepared in accordance herewith. Some further, non-limiting examples, of cross-linked proteins that may be prepared are, for illustration purposes, shown in FIGS. 3A-3D.

Figure 3A:
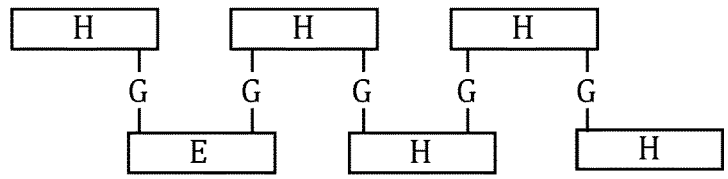
FIGS. 3A, 3B, 3C and 3D depict four different example configurations of cross-linked proteins. In each of FIGS. 3A, 3B, 3C and 3D, "H" represents a hemoglobin protein; "E"
Figure 3B:
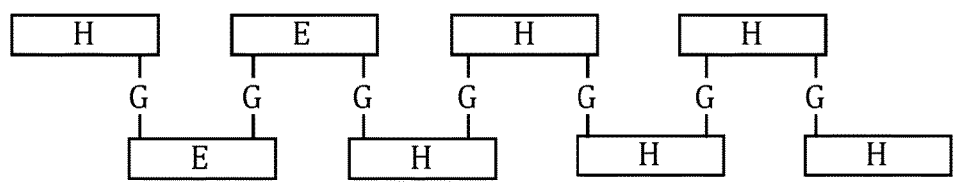
Figure 3C:
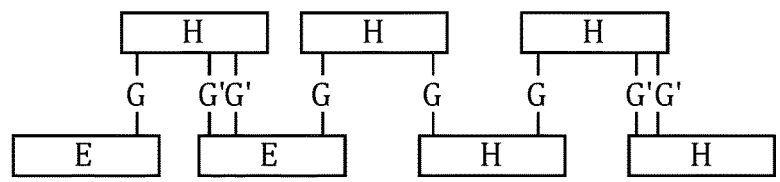
Figure 3D:
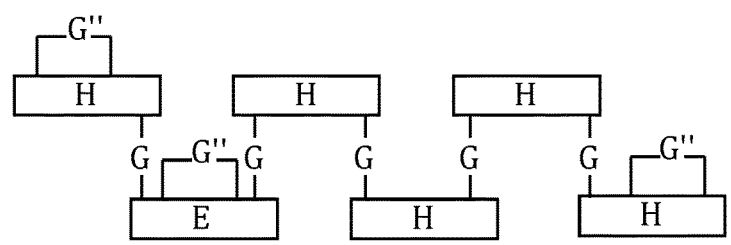

Referring now to FIGS. 3A-3D, shown therein are: in FIG. 3A, a cross-linked protein consisting of 6 proteins, intermolecularly cross-linked by cross-linkages (G), 5 hemoglobins (H) and 1 protein present in the endogenous non-hemoglobin protein complement (E); in FIG. 3B, a cross-linked protein consisting of 8 proteins, intermolecularly cross-linked by cross-linkages (G), 6 hemoglobins (H) and 2 proteins present in the endogenous non-hemoglobin protein complement (E); in FIG. 3C, a cross-linked protein consisting of 7 proteins, intermolecularly cross-linked by cross-linkages (G), 5 hemoglobins (H) and 2 proteins present in the endogenous non-hemoglobin protein complement (E), wherein multiple (2) cross-linkages (G') cross-link certain hemoglobins, and a hemoglobin to endogenous non-hemoglobin protein complement. It is noted in that in FIG. 3C, some proteins contain 3 cross-linkages, some proteins contain 2 cross-linkages and some proteins contain 1 cross-linkage; and in FIG. 3D, a cross-linked protein consisting of 6 proteins, intermolecularly cross-linked by cross-linkages (G), 5 hemoglobins (H) and 1 protein present in the endogenous non-hemoglobin protein complement (E), and 3 proteins intramolecularly cross-linked by a cross-linkage (G"). It is noted the cross-linkage (G") shown in association with hemoglobin (H) in FIG. 3D may represent a cross-linkage linking two of the 4 polypeptides constituting a hemoglobin molecule.

As hereinbefore mentioned, in one embodiment the cross-linkages formed can be reducible covalent bonds, for example Schiff bases. Accordingly, in the methodology of the present disclosure can comprise, in one embodiment, reacting the cross-linked proteins with a reducing agent to reduce reducible covalent cross-linkages and form reduced covalent linkages to thereby form a blood substitute preparation.

Referring now to FIG. 4, shown therein is a representation of an example chemical reaction between a reducible covalent cross-linkage, notably a Schiff base, and the reducing agent cyanoborohydride ($BH_3CN^-$) to form a reduced covalent cross-linkage. A chemical reaction between the Schiff base results in the reduction of the imine group and the formation a secondary amine group linkage and $BH_2CN$ (cyanoborane). The reaction may be conducted under a variety of conditions, including, for example, in a phosphate buffer, at neutral pH and 25° C.

In other embodiments, other reducing agents can be used in accordance herewith. Such reducing agents include, without limitation borohydride, dithionite, trimethylamine, t-butylamine, morpholine borane and pyridine borane, and salts of any of the foregoing, for example sodium salts.

In one embodiment, the preparation obtained following reduction can be reacted with an amino-group containing compound, for example lysine (its epsilon amino group) or arginine. The foregoing is deemed beneficial in certain embodiments as aldehydes that have failed to participate in a cross-linking reaction, can react with the amino-group containing compound, thus preventing further polyaldehyde reaction.

In accordance herewith, in another embodiment, the present disclosure provides a method of making a blood substitute preparation comprising hemoglobin, the method comprising:
(i) isolating erythrocytes from blood;
(ii) isolating a low purity erythrocyte protein fraction comprising hemoglobin protein and endogenous non-hemoglobin protein complement from the erythrocytes, the low purity erythrocyte protein fraction comprising from at least about 0.2% (mole/mole) up to about 20% (mole/mole) endogenous non-hemoglobin protein complement; and
(iii) contacting the low purity erythrocyte protein fraction with a polyaldehyde under reaction conditions permitting a chemical reaction between aldehyde groups of the polyaldehyde and amino groups of the proteins to form proteins cross-linked by a plurality of reducible covalent cross-linkages, the proteins comprising intermolecularly cross-linked hemoglobin proteins and hemoglobin intermolecularly cross-linked to the endogenous non-hemoglobin protein complement, to thereby form a blood substitute preparation.

In one embodiment, the cross-linked proteins can be reacted with a reducing agent to reduce the reducible covalent cross-linkages and form reduced cross-linkages thereby forming a blood substitute preparation.

To briefly recap, in a process according to a selected embodiment of the present disclosure a low purity erythrocyte protein fraction may be obtained. The low purity erythrocyte protein fraction includes hemoglobin protein, and endogenous non-hemoglobin protein complement from the erythrocytes. The endogenous non-hemoglobin protein complement within the low purity erythrocyte protein fraction constitutes from at least about 0.2% (mole/mole) up to about 20% (mole/mole). The low purity erythrocyte protein fraction is treated with reactant, wherein the reactant mediates the formation of cross-linked proteins. The cross-linked proteins comprise intermolecular cross-linkages between the hemoglobin protein molecules and intermolecular cross-linkages between the hemoglobin protein molecules and the endogenous non-hemoglobin protein complement, to thereby form a blood substitute preparation.

Next selected embodiments that can be used to prepare erythrocytes and low purity erythrocyte protein fractions are described. These selected embodiments are described with reference to FIG. 5 and FIG. 6.

Referring now to FIG. 5, shown therein is an example embodiment of a general scheme 500 for preparing a blood substitute preparation 525. Thus, in accordance with the embodiment shown in FIG. 5, whole blood 505 is used as a source material from which initially erythrocytes 510 are obtained. The erythrocytes 510 are then in turn used to obtain a low purity erythrocyte protein fraction comprising hemoglobin and endogenous non-hemoglobin protein complement 515. The low purity erythrocyte protein fraction 515 is treated to cross-link the proteins present therein using a polyaldehyde under reaction conditions that permit the formation of covalent cross-linkages. The reducible covalent cross-linkages are then reduced to form a blood substitute preparation comprising a reduced hemoglobin/endogenous non-hemoglobin protein complement 525, which can be used to formulate a finished blood substitute formulation 530.

In accordance with one aspect hereof, erythrocytes are isolated from blood. Suitable blood that may be used in accordance herewith includes vertebrate blood, including, without limitation, mammalian and avian blood, including without limitation, human blood, bovine blood, porcine blood, equine blood and ovine blood. Blood solutions may be collected from live or dead organisms and may be collected using any techniques and devices known to the art, including, for example, the methodologies described in U.S. Pat. Nos. 5,084,558 and 5,296,465. The blood may be fresh or from an older sample, for example expired blood from a blood bank institute. In addition, the blood may have been stored and/or frozen. It is preferred that the blood solution is screened for the presence of blood borne pathogens, for example where human blood is used, HIV and hepatitis B. Preferably, blood free of blood borne pathogens is selected for use in accordance with the methods of the present disclosure. Upon blood collection, it is preferred that an anti-coagulant is added to the blood to prevent blood clotting. Anti-coagulants that may be used include heparin, hirudin, sodium citrate, ethylenediaminetetraacetic acid. The anticoagulant may be provided as an aqueous solution or in particulate form.

In order to isolate erythrocytes from blood, any erythrocyte separation technique known to the art may be used. This includes the use of centrifugation and/or straining and filtering techniques to remove large blood aggregates (e.g. 50 μm and larger) and debris. Thus, one or more propylene 800 μm to 50 μm filters may be used. It is noted in this regard that erythrocytes are about 5-10 μm in size.

In some embodiments, the erythrocytes can be further isolated from blood by diafiltration using an isotonic solution, having a pH and osmolarity which preserves the integrity of the erythrocyte cellular membrane, for example, a sodium citrate (about 6.0 g/l) and sodium chloride (about 8.0 g/l) solution having an osmolarity of 285-315 mOsm. Acceptable diafiltration filters that can be used in accordance herewith include microporous membranes which substantially separate erythrocytes from smaller components for example, a modified polyethersulfone hollow fiber tangential flow filtration membrane obtainable from Spectrum labs. The isotonic solution can be added in batches or continuously, typically approximately at the same rate at which filtrate is lost. During this step, components of the blood solution smaller than erythrocytes, generally the plasma portion of the blood, including extracellular blood proteins, e.g. antibodies and serum albumins, are separated as filtrate from the erythrocytes, which are retained and continuously or batchwise added to the isotonic solution. Volumes of isotonic solution used may vary and may for example be at least 2×, 3×, 4×, 5×, 6× or 7× the volume of blood solution. Preferably sufficient volumes of isotonic solution are used to remove at least from about 90% to 95% (mole/mole) of blood plasma proteins and obtain a substantially pure erythrocyte preparation.

In one embodiment, erythrocytes can be isolated without the use of centrifugation techniques.

The techniques used to isolate erythrocytes from blood and to obtain a substantially pure erythrocyte preparation may be as desired, and include any techniques known to the art, including, for example the methods for isolating erythrocytes are described in U.S. Pat. No. 5,955,581, Thereafter the isolated erythrocytes can be lysed. Any technique for lysing erythrocytes known to the art may be used, including any mechanical lysis technique or chemical lysis technique, provided however that such technique does not substantially negatively affect the ability of hemoglobin to transport and release oxygen.

In one embodiment, the isolated erythrocytes can be lysed by subjecting the erythrocytes to a hypotonic shock to obtain an erythrocyte lysate. Suitable hypotonic solutions that may be used in accordance herewith include, for example, a phosphate buffer 3.75 mM, pH 7.2 or water which may be mixed with the red bloods cells, and the mixture may be incubated on ice, for example for 1 hour to obtain a lysed erythrocyte preparation.

In one embodiment, the low purity erythrocyte protein fraction can be obtained by subjecting an erythrocyte lysate to membrane filtration.

In one embodiment, the low purity erythrocyte protein fraction can be obtained by subjecting an erythrocyte lysate to tangential flow filtration.

In one embodiment, the erythrocyte lysate can be subjected to multiple tangential flow filtration steps. In one embodiment, the erythrocyte lysate can be subjected to three tangential flow separation steps wherein the first tangential flow separation step comprises the use of a membrane capable of separating viral contaminants and erythrocyte debris; the second tangential flow separation step comprises a high molecular weight cut-off of membrane; and the third tangential flow separation step comprises a low molecular weight cut-off membrane.

Referring now to FIG. 6, shown therein is an example embodiment of a system 600 comprising tangential flow devices 620, 640 and 645 connected via a tubular line 660 comprising various section 660$a$, 660$b$, 660$c$, 660$d$, 660$e$, 660$f$ and 660$g$ through which lysate 665 supplied from reservoir 610 is pumped using pump 505. The pump used may, for example be a peristaltic-type pump or a diaphragm-type pump. Reservoir 610 may be maintained under a low oxygen environment, for example by blanketing the reservoir with nitrogen gas, and further is preferably sealed to prevent contamination. Upon exiting reservoir 610 via exit reservoir exit 611, lysate 665 is directed, via section 660$a$ and 660$b$ of tubular line 660, towards tangential flow device 620 having a polysulfone 50 nm hollow fiber membrane 665, and enters the tangential flow device 620 via tangential flow device entry 680. Within tangential flow device 620, lysate 665 is filtered through membrane 665 to yield: (i) a filtrate exiting the tangential flow device 620 via tangential flow device filtrate exit 625 and (ii) a rententate exiting the tangential flow device 620 via tangential flow device rententate exit 615. The retentate returns via section 660$c$ of tubular line 660 towards reservoir 610 and enters the reservoir 610 at reservoir entry 612 for recirculation. The filtrate, via section 660$d$ of the tubular line 660 is directed towards tangential flow device 640, enters tangential flow device 640 via tangential flow device entry 690, and is filtered through 500 kDa molecular weight hollow fiber polysulfone membrane 670 to yield: (i) a filtrate, exiting the tangential flow device 640 via tangential flow device filtrate exit 635, and (ii) a rententate exiting the tangential flow device 640 via tangential flow device retentate exit 630. The retentate is re-circulated via section 660$e$ of the tubular line 660. The filtrate flows, via section 660$f$ of the tubular line 660 towards tangential flow device 645, enters tangential flow device 645 via tangential flow device entry 695, and is filtered through 50 kDa molecular weight hollow fiber polysulfone membrane 675 to yield: (i) a filtrate which is discharged from the tangential flow device 645 via tangential flow device filtrate exit 650 and (ii) a rententate exiting the tangential flow device 645 via tangential flow device retentate exit 655. The retentate is re-circulated via section 660$g$ of the tubular line 660. The filtrate discharged from tangential flow device 645 may be disposed. The retentate comprising the low purity erythrocyte protein fraction comprising hemoglobin and endogenous non-hemoglobin protein complement is obtained. Thus, the performance of tangential flow filtration in accordance with the foregoing example embodiment results in the retention of a low purity erythrocyte protein fraction comprising hemoglobin and endogenous non-hemoglobin protein complement in the retentate following the third tangential flow step while smaller sized contaminants are obtained in the filtrate of the third step.

In one embodiment, the endogenous non-hemoglobin protein complement can comprise a protein selected from the group consisting of superoxide dismutase and carbonic anhydrase.

In one embodiment, the endogenous non-hemoglobin protein complement can comprise from about 0.2% (mole/mole) to about 15% (mole/mole) carbonic anhydrase.

The foregoing low purity erythrocyte protein fraction can be used to chemically modify the proteins therein in order to obtain a blood substitute preparation comprising hemoglobin cross-linked to endogenous non-hemoglobin protein complement.

In one embodiment, the preparation obtained following the performance of the chemical modification step can be used to prepare a finished blood substitute formulation. Thus, in another aspect, the present disclosure provides, in one embodiment, a method for preparing a finished blood substitute formulation comprising hemoglobin, the method comprising:

(i) providing a low purity erythrocyte protein fraction comprising hemoglobin protein molecules and endogenous non-hemoglobin protein complement obtainable from erythrocytes, the low purity erythrocyte protein fraction comprising from at least about 0.2% (mole/mole) up to about 20% (mole/mole) endogenous non-hemoglobin protein complement, the low purity erythrocyte protein fraction modified with a reactant capable of chemically modifying the proteins in the protein fraction, wherein the reactant mediates the formation of cross-linked proteins comprising intermolecular cross-linkages between the hemoglobin protein molecules and intermolecular cross-linkages between the hemoglobin protein molecules and the endogenous non-hemoglobin protein complement, to thereby form a blood substitute preparation; and (ii) formulating the blood substitute preparation with at least one other ingredient suitable to form a finished blood substitute formulation.

In one embodiment, the finished blood substitute formulation can be a formulation for in-vivo use.

In one embodiment, the finished blood substitute formulation can be a formulation for ex-vivo use.

In one embodiment, the blood substitute preparation can be contacted with at least one other ingredient suitable for use in finished blood substitute preparation, notably a diluent, carrier or excipient. The blood substitute preparation and diluent, carrier or excipient are mixed, homogenized or prepared, preferably until a homogenous mixture of the diluent, carrier or excipient and blood substitute preparation is formed, wherein such mixture is suitable for use as a blood substitute formulation. The diluent, carrier or excipient may be any suitable diluent, carrier or excipient, and may the diluent, carrier or excipient may be provided in any form, including, for example, as a solution, suspension, gel, liquid, solid, powder, or crystal. The quantity of the diluent, carrier or excipient can vary. Typically, a plurality of ingredients is provided, for example at least 2, 3, 4, 5, 6, 7, 8, 9, 10 or more ingredients, in addition to the blood substitute preparation, to prepare the finished blood substitute formulation. In embodiments hereof that include a plurality of ingredients, such ingredients may be mixed sequentially or simultaneously.

In one embodiment, the additional ingredients include compounds normally found in blood, for example, ions normally found in blood, including calcium ions; chloride ions; sodium ions; magnesium ions; phosphate ions; or mixtures thereof, each of which can be provided in a variety of chemical forms, including, for example sodium chloride, and a variety of formulations, for example in the form of a saline solution. Other ingredients that can be included to prepare a finished blood preparation are amino acids; reducing agents, for example glutathione, ascorbic acid, or n-acetyl cysteine; colloids such as hydroxyethyl starch or albumin; sugars, including monosaccharides or disaccharides, such as glucose or lactobionic acid; or mixtures thereof. In some embodiments, even pharmacological compounds capable of ameliorating a disease state or medical condition can be included. Thus, for example, in some embodiments, insulin can be included as a pharmacological ingredient.

In one embodiment, in order to formulate the blood substitute preparation obtained following chemical modification step, the preparation is subjected to diafiltration using an excipient buffer to prepare a finished blood substitute formulation, using for example a modified lactated Ringer's modified with N-acetyl-L-cysteine (NAC) (NaCl (115 mmol/l; KCl 4 mmol/l; NaOH 13 mmol/l; sodium lactate (27 mmol/l) and N-acetyl-L-cysteine (2 g/l) to perform the diafiltration.

In one embodiment, the performance of a diafiltration step removes and replaces the solution in which the protein is suspended, including for example a reactant glutaraldehyde and reductant, however the protein constituents obtained following the performance of the reduction are substantially retained in the finished blood substitute formulation.

In one embodiment, the preparation obtained following the chemical modification step is subjected to diafiltration using a filter and conditions that result in the removal of proteins having a molecular weight of about 100 kDa or less from the preparation in order to prepare a finished blood substitute formulation. In one embodiment, the preparation obtained following reduction is subjected to diafiltration using a filter and conditions that result in the removal of proteins having a molecular weight of less than about 300 kDa, about 400 kDa, about 500 kDa, about 600 kDa, about 700 kDa, about 800 kDa, about 900 kDa, about 1,000 kDa or about 1,100 kDa from the preparation. The foregoing thus results in the removal from the blood substitute preparation of proteins having a lower molecular weight, which generally will be proteins which have not been cross-linked or cross-linked to a smaller degree, and thus the relative concentration of cross-linked hemoglobin present in the preparation can be increased. In this manner a blood substitute preparation may be obtained in which at least about 90% (mole/mole), about 91% (mole/mole), about 92% (mole/mole), about 93% (mole/mole), about 94% (mole/mole), about 95% (mole/mole), about 96% (mole/mole), about 97% (mole/mole), about 98% (mole/mole), or about 99% (mole/mole) of hemoglobin is cross-linked. The diafiltration buffer used in some embodiments can be an excipient including, for example a modified lactated Ringer's modified with N-acetyl-L-cysteine (NAC) (NaCl (115 mmol/l; KCl 4 mmol/l; NaOH 13 mmol/l; sodium lactate (27 mmol/l) and N-acetyl-L-cysteine (2 g/l).

In one embodiment, the method of the present disclosure further includes the performance of a deoxygenation step.

In one embodiment, the low purity erythrocyte protein fraction is deoxygenated. Any deoxygenation methodology may be used including any chemical deoxygenation methodology. Preferably a gas exchange filtration methodology is used to achieve such deoxygenation, using an inert gas, for example nitrogen, argon or helium. In some embodiments deoxygenation can result in hemoglobin having a P50 of from about 30-50 mm Hg. In preferred embodiments, deoxygenation can result in hemoglobin having a P50 of about 40 mm Hg.

In one embodiment, the erythrocytes can be deoxygenated and all subsequent steps are performed under low oxygen conditions.

In one embodiment, the finished blood substitute formulations may be stored for shorter or longer periods of time, for example, from 1-2 days up to 1 year or more. Finished blood substitute formulations are preferably stored in sterile, sealed containers, for example sealed glass containers, stainless steel containers or storage bags, having a low oxygen environment. Storage containers are further preferably impermeable to the transfer of water in order to prevent evaporation of water and concentration of the formulation. In order to achieve a low oxygen environment storage containers may be blanketed with, for example, a nitrogen atmosphere prior to sealing. In some embodiments, in order to prevent auto-oxidation the finished blood substitute formulation is treated with carbon monoxide. In order to store the blood substitute formulations, the containers may be refrigerated (0° C. to 4° C.) for storage or blood may be frozen and stored in a freezer, for example from −20° C. to −80° C.

Blood Substitute Preparations and Finished Blood Substitute Formulations

In another aspect, the present disclosure further provides novel blood substitute preparations. Accordingly, the present disclosure provides, in at least one embodiment, a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising endogenous erythrocyte endogenous non-hemoglobin protein complement of at least about 0.2% (mole/mole) and up to about 20% (mole/mole).

In at least one embodiment, at least about 90% (mole/mole) of the hemoglobin protein molecules in the erythrocyte protein fraction can be cross-linked, so that the average molecular mass of cross-linked proteins is at least about 300 kDa.

In one embodiment, the endogenous non-hemoglobin protein complement can comprise carbonic anhydrase, wherein the carbonic anhydrase comprises from about 0.2% (mole/mole) to 15% (mole/mole) of the endogenous non-hemoglobin protein complement.

In one embodiment, the cross-linkages can be reducible cross-linkages.

In one embodiment, the cross-linkages can be Schiff bases.

In one embodiment, the cross-linkages can be reduced Schiff bases.

In one embodiment, the cross-linkages can be reduced Schiff bases having been formed by reacting proteins in the low purity erythrocyte fraction with a polyaldehyde to form Schiff bases, and subsequent reduction of the Schiff bases.

In one embodiment, the polyaldehyde can be glutaraldehyde.

In one embodiment, the blood substitute preparation can exhibit a P50 of from about 30 mm Hg to about 50 mm Hg. In one embodiment, the blood substitute preparation exhibits a P50 of about 36 mm Hg.

In one embodiment, the blood substitute preparation can exhibit a total hemoglobin concentration of from about 10 to about 12 g/dL. In one embodiment, the blood substitute preparation can exhibit a total hemoglobin concentration of about 11 g/dL.

In one embodiment, the blood substitute preparation can comprise an endotoxin load of less than about 5 EU/ml, 4 EU/ml, 3 EU/ml, 2 EU/ml or 1 EU/ml.

In one embodiment, the blood substitute preparation can comprise hemoglobin wherein methemoglobin comprises less than about 10% mole/mole, less than about 9% mole/mole, less than about 8% mole/mole, less than about 6% mole/mole, less than about, less than about 5% mole/mole, or less than about 1% mole/mole of the total hemoglobin constituent.

In one embodiment, the blood substitute preparation can comprise a methemoglobin concentration of between about 4.5% and about 6.0%.

In one embodiment, the blood substitute preparation can comprise a methemoglobin concentration of about 5.8%

In one embodiment, the blood substitute preparation can exhibit a Hill number of about 1.2.

In one embodiment, the blood substitute preparation can exhibit a viscosity of between about 12 and about 18 centipoise, or between about 13 and about 17 centipoise.

In one embodiment, the blood substitute preparation can exhibit a viscosity of about 15 centipoise.

In one embodiment, the blood substitute preparation can exhibit a colloid osmotic pressure (COP) of between about 5 mm Hg and about 11 mm Hg, or between about 6 mm Hg and about 10 mm Hg, or between about 7 mm Hg and about 9 mm Hg.

In one embodiment, the blood substitute preparation can exhibit a colloid osmotic pressure (COP) of about 8 mm Hg.

It is noted that when formulations comprising the preparations of the present disclosure are administered to a subject in need thereof limited or no narrowing of the blood vessels may be observed, a physiological process also referred to as vasoconstriction. Furthermore, limited or no leakage of hemoglobin from the blood vessels may be observed, a physiological process also referred to as extravasation. Without wishing to be bound by theory, it is believed that the relatively high viscosity and low COP of the blood substitute preparations of the present disclosure contribute to the achievement of limited or no vasoconstriction and/or extravasation. Thus, upon administration of the blood preparations of the present disclosure normal or near normal physiological conditions with respect to extravasation and vasoconstriction may be maintained.

In one embodiment, the blood substitute preparation can exhibit limited formation of reactive oxygen species, notably hydrogen peroxide ($H_2O_2$), for example, less than 8,000 pmol/min/mg, less than 7,000 pmol/min/mg or less than 6,000 pmol/min/mg. The formation of a limited amount of reactive oxygen species is deemed to be a beneficial attribute of the preparations of the present disclosure since reactive oxygen species can damage the endothelial glycocalyx of blood vessels.

In one embodiment, all, or substantially all, hemoglobin protein molecules present in the blood substitute preparation can comprise at least one, at least two, at least three, at least four, or at least five covalent cross-linkages.

In one embodiment, at least about 90% (mole/mole), at least about 95% (mole/mole), at least about 96% (mole/mole), at least about 97% (mole/mole), at least about 98% (mole/mole), at least about 99% (mole/mole) of hemoglobin molecules present in the blood substitute preparation can be cross-linked via at least one covalent cross-linkage.

In another aspect, the present disclosure provides, in one embodiment, a finished blood substitute formulation comprising a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole).

In one embodiment, at least about 90% (mole/mole) of the hemoglobin protein molecules in the erythrocyte protein fraction can be cross-linked, so that the average molecular mass of cross-linked proteins is at least about 300 kDa.

In one embodiment, the at least one other ingredient can be an excipient, diluent or carrier In at least one embodiment, the finished blood substitution formulation can comprise a blood substitute preparation made according to any of the methods of the present disclosure.

Uses of Blood Substitute Preparations

In another aspect, the present disclosure provides, in one embodiment, a use of a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole) to prepare a finished blood formulation for in-vivo use.

In one embodiment, at least about 90% (mole/mole) of the hemoglobin protein molecules in the erythrocyte protein fraction can be cross-linked, so that the average molecular mass of cross-linked proteins molecules is at least about 300 kDa.

In one embodiment, the endogenous non-hemoglobin protein complement can comprise carbonic anhydrase, wherein the carbonic anhydrase comprises from about 0.2% (mole/mole) to 15% (mole/mole) of the endogenous non-hemoglobin protein complement.

In one embodiment, the present disclosure provides a use of a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole) to prepare a finished blood formulation for ex-vivo use.

In one embodiment, at least about 90% (mole/mole) of the hemoglobin protein molecules in the erythrocyte protein fraction can be cross-linked, so that the average molecular mass of cross-linked proteins is at least about 300 kDa.

In one embodiment, the endogenous non-hemoglobin protein complement can comprise carbonic anhydrase, wherein the carbonic anhydrase comprises from about 0.2% (mole/mole) to 15% (mole/mole) of the endogenous non-hemoglobin protein complement.

The blood substitute formulation may be administered to and received by any subject in need thereof. In some embodiments, the blood substitute formulation is received by a vertebrate including a mammal, such as a primate, a dog, a cat, a horse, a pig, a cow, a goat, a sheep, and further including a bird, fish or a reptile. In further embodiments, the blood substitute formulation is received by a human. Furthermore, the blood substitute formulation may be received at any phase of life, including prenatal fetuses, and post-natal new-borns.

The blood-substitute formulation of the present disclosure can be administered into the circulatory system by injection into the circulatory system of a vertebrate. Examples of injection techniques include intravascular injections, such as intravenous and intra-arterial injections, and intracardiac injections, and further include intraperitoneal injections, subcutaneous injections, in a manner that permits transport of the blood substitute by the lymph system into the circulatory system, injections into the bone marrow by means of a trocar or catheter. Preferably, the blood substitute formulation of the present disclosure can be administered intravenously. The blood substitute formulation of the present disclosure can be administered therapeutically, to treat hypoxic tissue within a vertebrate resulting from many different causes including reduced erythrocyte flow in a portion of, or throughout, the circulatory system as a result of myocardial infarction, stroke, anemia, trauma or shock, including, anaphylactic shock, septic shock or allergic shock. The blood substitute formulation of the present disclosure further can be used in replacement of blood as a result of acute hemorrhage, during surgical operations, in resuscitation procedures. The blood substitute formulation can be also administered prophylactically to prevent oxygen-depletion of tissue within a vertebrate, resulting from a possible or anticipated reduction in erythrocyte flow.

The therapeutic amounts of the blood substitute formulation administered may vary. The term "therapeutically effective amount," for the purposes of the present disclosure, refers to the amount of blood substitute formulation which is effective to achieve its intended purpose. While individual needs vary, determination of optimal ranges for effective amounts of a blood substitute formulation to be administered is within the skill of one in the art. Research animals such as dogs, rats or primates can be used to determine dosages. Generally, dosages required to provide effective amounts of the formulation or preparation, and which can be adjusted by one of ordinary skill in the art, will vary, depending on the age, health, physical condition, sex, weight, extent of condition of the recipient, frequency of treatment and the nature and scope of the desired effect for a particular patient or animal, as can be determined by one of ordinary skill in the art using conventional considerations, (e.g. by means of an appropriate, conventional pharmacological or veterinary protocol).

In another aspect, the present disclosure provides, in one embodiment a method of delivering a therapeutically effective amount of a finished blood substitute formulation comprising a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole), to a subject in need thereof.

In another aspect, the present disclosure provides, in one embodiment, a use of a finished blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole) for in-vivo administration.

In at least one embodiment, the present disclosure provides, one embodiment, a use of a finished blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to endogenous non-hemoglobin protein complement, the low purity protein fraction comprising erythrocyte endogenous non-hemoglobin protein complement of at least about 0.2% (mole/mole) and up to about 20% (mole/mole) for ex-vivo administration.

In one embodiment, the blood substitute formulation of the present disclosure is used to maintain the oxygen content of an organ or tissue ex-vivo in order to preserve an organ or tissue, for example, when organs are stored for later transplantation to a patient, or for reimplantation in a patient, or when organs or tissue require transportation. Individual organs that may be used in this regard include, without limitation liver, kidney, heart, lung, intestine and pancreas. Examples of tissue transplants include composite tissue allotransplants, e.g. limbs, face. In some embodiments, the organs or tissue are preserved in static mode. In other embodiments, the organs are preserved in dynamic mode. In static mode the organs are bathed in a solution comprising the blood substitute formulation of the present disclosure. In dynamic mode, the organ is perfused using the blood substitute formulation of the present disclosure and one or more mechanical devices including, for example, a pump system, and devices for regulating temperature.

In one embodiment, the blood substitute formulations of the present disclosure can be used to maintain organs for research and development purposes, for example, for the discovery of biomarkers or for use of organ tissue as a bioreactor.

In addition to preservation of individual tissues or organs, the compositions of the present disclosure may also be used for whole body preservation of living donors, including brain-dead individuals, or cadavers.

dismutase.

As now can be appreciated, a blood substitute preparation can be prepared according to the methods of the present disclosure, which avoids obtaining a high purity hemoglobin preparation, and the complicated operational processes associated therewith. The blood substitute preparation can be applied in many clinical processes.

Of course, the above described example embodiments of the present disclosure are intended to be illustrative only and in no way limiting. The described embodiments are susceptible to many modifications of composition, details and order of operation. The invention, rather, is intended to encompass all such modifications within its scope, as defined by the claims, which should be given a broad interpretation consistent with the description as a whole.

EXAMPLES

Hereinafter are provided examples of further specific embodiments for performing the methods of the present disclosure, as well as embodiments representing the compositions of the present disclosure. The examples are provided for illustrative purposes only, and are not intended to limit the scope of the present disclosure in any way.

Example 1—Blood Substitute Preparation Comprising a Low Purity Erythrocyte Blood Protein Fraction Cross-Linked with Glutaraldehyde A low purity erythrocyte protein fraction was prepared from erythrocytes as follows. Packed red blood cells obtained from an authorized distributor that were first 1) washed via 6 diafiltration exchanges of normal saline across a 0.45 µM hollow fiber filter, and then 2) lysed with a further 6 diafiltration exchanges of purified water, 3) then the filtrate fraction containing proteins purified with 6 diafiltration exchanges of phosphate buffer across a 500 kDa hollow fiber filter, 4) and the collected protein in the filtrate further washed with 6 diafiltration exchanges of phosphate buffer and n-acetyl cysteine across a 10 kDa hollow fiber filter, keeping the retentate. During the last step, the solution was concurrently deoxygenated with a gas exchange cartridge and nitrogen. The resulting protein solution (2 g/dL) was reacted with glutaraldehyde at a final concentration of 1.25 g/l) for three hours and then reduced with cyanoborohydride ($BH_3CN$) and was put into a lactated Ringer's solution with n-acetyl cysteine such that the glutaraldehyde and cyanoborohydride were removed via diafiltration to thereby obtain a low purity blood substitute preparation. The concentration of endogenous non-hemoglobin protein complement in the protein preparation was estimated to be between about 0.2 mole/mole and about 20% mole/mole, based on an SDS gel evaluation. All steps were performed at room temperature. The blood substitute preparation was then diluted and placed in a stoppered cuvette such that it could be monitored spectrophotometrically. No effort was made to remove ambient oxygen, and the expected result was that the hemoglobin preparation in the presence of ambient oxygen would oxidize to methemoglobin, a physiologically inactive form of hemoglobin. A change would result in a concomitant characteristic spectral shift that can be easily detected and measured. The spectra initially observed were the expected ones for oxygenated hemoglobin. Surprisingly, however, the hemoglobin in the blood substitute preparation was not observed to undergo substantial oxidation for a period 48 hours, and a shift abruptly to the deoxygenated form of hemoglobin was not observed. The foregoing observation indicates that 1) the overall oxidation level of the product remained substantially constant, and 2) the available oxygen was slowly consumed in the stoppered cuvette until there was none bound to the hemoglobin. This is advantageous for an oxygen delivery solution where oxidation limits its effectiveness.

Example 2—In-Vivo Administration of Blood Substitute Preparations

A blood substitute preparation was prepared as described in Example 1. Using a hemorrhagic shock (HS) model blood was withdrawn from rats (3) to model blood loss, and then administered the blood substitute preparation and Lactated Ringers Solution (LRS) as a control. Interstitial oxygen pressure was recorded as a function of time. The results were graphed and are shown in FIG. 7. Results for the LRS solution are labelled LRS-Avg. Results for the blood substitute preparation are labeled VIR-VET Avg. As can be seen in FIG. 7, initially following the injury (t=−25 minutes), the interstitial oxygen pressure rapidly dropped to about 0 mm Hg. Administration of LRS and the blood substitute preparation lead to an initial recovery of interstitial oxygen pressure peaking at about 18 mm Hg for rats treated with LRS, and about 38 mm Hg for rats treated with the blood substitute preparation. Thereafter a rapid decline in interstitial oxygen pressure was observed, reaching 0 mm Hg at about t=15 minutes in animals treated with LRS. The decline in interstitial oxygen pressure in rats treated with the blood substitute preparation was more gradual and reached 0 mm Hg at about t=90 min.

In the same experiment, survival time of the rats following administration was monitored. The results were graphed and shown in FIG. 8. Results for the LRS solution are labelled LRS. Results for the blood substitute preparation are labeled VTB. As can be seen in FIG. 8, 100% of the rats having been administered LRS had died 25 minutes following administration of LRS. By contrast, rats having been administered the blood substitute preparation survived substantially longer with 100% of the rats having died 98 minutes following administration of the blood substitute preparation.

In a separate experiment a model rat was infused with a 10% blood substitute preparation prepared as described in Example 1, and microvascular responses in muscle tissue was evaluated microscopically. Results are shown in FIG. 9. As can be seen in FIG. 9, no substantive change in vascular structure was observed immediately upon administration or 120 minutes following administration of the blood substitute preparation.

Example 3—Ex-Vivo Administration of Blood Substitute Preparations

A swine liver was obtained and perfused with a continuously oxygenated blood substitute preparation at 21° C. with machine perfusion for a period of 12 hours using a substitute preparation prepared as described in Example 1. Liver biopsies of the perfused liver and liver prior to perfusion were taken and stained by heamotoxylin and eosin stain.

Microscopic images are shown in FIGS. 10A and 10B. Shown are images of hepatic tissue at different magnifications (labeled 10× and 20×). The microscopic images of the hepatic tissue in FIGS. 10A and 10B were microscopically evaluated by a pathologist in a blind test. The pathologist was unable to distinguish between the biopsy obtained from the perfused liver, and the biopsy of the liver prior to perfusion.

Example 4—Characterization of Blood Substitute Preparations—Protein Constituents A blood substitute preparation was prepared as described in Example 1. The proteins were evaluated using SDS polyacrylamide gelelectrophoresis (PAGE) and size exclusion chromatography. The results are show in FIG. 11 (SDS PAGE) and FIGS. 12A-12C (size exclusion chromatography). As can be seen in FIG. 11, the blood substitute preparation contains in addition to some hemoglobin (purified hemoglobin samples shown in lanes 2 and 3; two different lots), proteins of a molecular mass substantially higher than the molecular mass of hemoglobin (lanes 4-6). Lane 4 represents a non-cross-linked erythrocyte protein fraction from which proteins smaller than 300 kDa have been removed by diafiltration. Lanes 5 and 6 represent two lots of glutaraldehyde cross-linked protein preparations. The higher molecular mass proteins in lanes 5-6 represent cross-linked hemoglobin molecules and hemoglobin molecules cross-linked to endogenous non-hemoglobin protein complement. FIGS. 12A-C show the average molecular mass of purified hemoglobin, and is estimated to be about 16 kDa which corresponds with the individual monomers (FIG. 12A) and the average molecular mass of the cross-linked protein in the blood substitute preparation (i.e. cross-linked hemoglobin and hemoglobin-cross-linked to endogenous non-hemoglobin protein complement), which is estimated to be about 1,000 kDa (FIG. 12B). Molecular size markers are shown for comparison (FIG. 12C). Furthermore, the amount of non-cross-linked hemoglobin present in the blood substitute preparation is estimated to be less than 10% mole/mole.

Example 5—Characterization of Blood Substitute Preparations—Physicochemical Attributes A blood substitute preparation was prepared as described in Example 1, and evaluated from a physicochemical standpoint. The physicochemical parameters that were evaluated were: (i) concentration total hemoglobin; (ii) concentration methemoglobin; (iii) pH: (iv) osmolality: (v) molecular mass: (vi) concentration hemoglobin dimer; (vii) partial pressure of oxygen (P50); (viii) Hill number, (ix) viscosity; and (x) colloid osmotic pressure (COP). Table 1 shows the results obtained.

TABLE 1

Physicochemical attributes of blood substitute preparation (average +/− standard deviations; 3 lots)

| Property | Values | SD (+/−) |
|---|---|---|
| Total Hb (g/dl) | 11 | 0.3 |
| MetHb (%) | 4.7 | 0.3 |
| pH | 7.5 | 0.03 |
| Osmolality (mOsmS) | 305 | 4.6 |
| Molecular Mass (Million Daltons) | ~1.1 | — |
| Hemoglobin-Dimer (%) | <3 | 0.3 |
| p50 (mm Hg)* | 36 | 1.2 |
| Hill Number* | 1.2 | 0.03 |
| Viscosity (cPs) | 15 | — |
| COP (mm Hg) | 8 | — |

*Measured at [Hb] = 1 mg/ml in Hemox buffer, pH 7.4, 37° C.

The obtained physicochemical attributes of a blood substitute preparation prepared as described in Example 1 were also compared with various blood substitute preparations known to the art, including (i) pRBCs; (ii) aaHb, see: Creteur, J. et al, "Diaspirin cross-linked hemoglobin improves oxygen extraction capabilities in endotoxic shock', J Appl Physiol, 2000, 89: 1437-1444; (iii) Hemospan, see: Vandegriff K D et al., "MP4, a new non-vasoactive PEG-Hb conjugate", Transfusion, 2003: Vol 43, Issue 4, Pages 509-16, and Vandegriff K D and Winslow R. M., "Hemospan: Design Principles for a New Class of Oxygen Therapeutic" Artif Organs, 2009; Vol 33, Pages 133-138; (iv) Oxyglobin, see: presentation by W. R. Light, "Oxygen Transport: The New Physiology" at ESCVS International Congress, 2011; (v) Hemopure, see: presentation by W. R. Light, "Oxygen Transport: The New Physiology" at ESCVS International Congress, 2011; and (vi) OxyVita (hb), see: Harrington, J. P. and Wollocko, H. "Molecular Design Properties of OxyVita Hemoglobin, a New Generation Therapeutic Oxygen Carrier: A Review", J. Funct. Biomaterial. 2011, 2, 414-424. The results are shown in Table 2, wherein VIR-HBOC denotes a preparation prepared according to the method described in Example 1.

TABLE 2

Comparison of physicochemical attributes of various blood substitute preparations

| Property | VIR-HBOC | pRBCs | aaHB | Hemospan | Oxyglobin | Hemopure | OxyVita Hb |
|---|---|---|---|---|---|---|---|
| Total Hb (g/dl) | 11 | ~18 | 10 | 4.4 | 13 | 13 | 6 |
| MetHb (%) | 5.8 | 5 | 6.3 | <10 | <10 | <10 | <5 |
| pH | 7.4 | 7.5 | 7.4 | 7.4 | 7.7 | 7.7 | 7.5 |
| Osmolality (mOsmS) | 305 | 310 | | 310 | 300 | 300 | |
| Molecular Mass (kD) | Avg ~1000 | Cell | ~65 | ~10 | Avg ~180 | Avg ~250 | Avg ~1700 |
| p50 (mm Hg) | 36* | ~14* | 32 | 4 | 40 | 40 | 6 |
| Hill Number | 1.2* | ~2.6* | | 1.6 | 1.6 | 1.6 | 1.1 |
| Viscosity (cPs)** | 15 | ~13.4 | ~1.5 | 4 | 2.1 | 2.4 | 1.5 |
| COP (mm Hg) | 8 | ~5 | 43 | 78 | 40 | 26 | 3 |

*Measured at [Hb] = 1 mg/ml in Hemox buffer, pH 7.4, 37° C.

Example 6—Formation of Reactive Species within Blood Substitute Preparations

A blood substitute preparation was prepared as described in Example 1 and used to ex-vivo perfuse three swine livers for a period of time at 21° C. The level of reactive oxygen species (ROS) ($H_2O_2$) formation was evaluated following incubation for 3 hrs, 6 hrs and 9 hrs. The results are shown in in FIG. 13, wherein the bars denoted by P1 represent the level of $H_2O_2$ production when the livers are present in-vivo prior to harvesting, the bars denoted by BT represent the level of $H_2O_2$ production upon initial perfusion, and the bars denoted by 3 hr, 6 hr, and 9 hr, the level of $H_2O_2$ production following perfusion for 3 hours, 6, hours and 9 hours respectively. As can be seen $H_2O_2$ production does not increase during perfusion of the each of the livers and remains in all instances below about 7,500 pmol/min/mg.

The invention claimed is:

1. A finished blood substitute formulation comprising a blood substitute preparation comprising a low purity erythrocyte protein fraction comprising chemically modified cross-linked proteins comprising hemoglobin protein molecules and endogenous non-hemoglobin protein complement, the hemoglobin protein molecules intermolecularly cross-linked via cross-linkages, and the hemoglobin protein molecules intermolecularly cross-linked via cross-linkages to the endogenous non-hemoglobin protein complement, the low purity protein fraction comprising about 0.2% (mole/mole) to about 20% (mole/mole) of the endogenous non-hemoglobin protein complement, wherein the endogenous non-hemoglobin protein complement comprises carbonic anhydrase.

2. The finished blood substitute preparation according to claim 1, wherein about 90% (mole/mole) of the hemoglobin protein molecules in the erythrocyte protein fraction are cross-linked, wherein the average molecular mass of cross-linked proteins is at least 300 kDa.

3. The finished blood substitute preparation according to claim 1, wherein about 90% (mole/mole) of the hemoglobin protein molecules in the erythrocyte protein fraction are cross-linked, wherein the average molecular mass of cross-linked proteins is at least 1,000 kDa.

4. The finished blood substitute preparation according to claim 1, wherein the carbonic anhydrase, comprises about 0.2% (mol/mole) to about 15% (mole/mole) of the endogenous non-hemoglobin protein complement.

5. The finished blood substitute preparation according to claim 1, wherein the cross-linkages are reducible covalent cross-linkages.

6. The finished blood substitute preparation according to claim 5, wherein the reducible covalent cross-linkages are Schiff bases.

7. The finished blood substitute preparation according to claim 6, wherein the reduced covalent cross-linkages are secondary amines.

8. The finished blood substitute preparation according to claim 5, wherein the cross-linkages are reduced Schiff bases.

9. The finished blood substitute preparation according to claim 8, wherein the cross-linkages are reduced Schiff bases having been formed by reacting proteins in the low purity erythrocyte fraction with a polyaldehyde to form a Schiff base, and subsequent reduction of the Schiff base.

10. The finished blood substitute preparation according to claim 9, wherein the polyaldehyde is glutaraldehyde.

11. The finished blood substitute preparation according to claim 1, further comprising at least one additional ingredient suitable to form a finished blood substitute formulation.

12. The finished blood substitute preparation according to claim 11, wherein the at least one additional ingredient is an excipient, diluent, or carrier.

13. The finished blood substitute preparation according to claim 1, wherein the blood substitute preparation is a formulation suitable for in-vivo use and/or for ex-vivo use.

14. The finished blood substitute preparation according to claim 13, wherein the blood substitute preparation comprises at least one of a concentration of about 10 grams/deciliter to about 12 grams/deciliter of total hemoglobin, a pH of about 7.5, a partial pressure of oxygen (p50) of about 30 mmHg to about 50 mmHg, and a viscosity of about 12 cPs to about 18 cPs.

15. The finished blood substitute preparation according to claim 1, wherein the blood substitute preparation comprises at least one of a concentration of about 10 grams/deciliter of total hemoglobin, a pH of about 7.7, a partial pressure of oxygen (p50) of about 32 mmHg, and a viscosity of about 12 cPs.

16. The finished blood substitute preparation according to claim 1, wherein the endogenous non-hemoglobin protein complement further comprises superoxide dismutase.

* * * * *